(12) United States Patent
Huang et al.

(10) Patent No.: US 7,541,392 B2
(45) Date of Patent: Jun. 2, 2009

(54) MATERIALS LEADING TO IMPROVED DENTAL COMPOSITES AND DENTAL COMPOSITES MADE THEREFROM

(75) Inventors: Donald Da-Jen Huang, Newark, DE (US); Gary Delmar Jaycox, West Chester, PA (US); Carl Brent Douglas, Boothwyn, PA (US); Lech Wilczek, Wilmington, DE (US); Gordon Mark Cohen, Wynnewood, PA (US); Charles J. Brandenburg, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 550 days.

(21) Appl. No.: 11/225,228

(22) Filed: Sep. 13, 2005

(65) Prior Publication Data

US 2006/0058414 A1 Mar. 16, 2006

Related U.S. Application Data

(60) Provisional application No. 60/609,588, filed on Sep. 14, 2004.

(51) Int. Cl.
*A61K 6/08* (2006.01)
*A61K 6/083* (2006.01)
*A61K 6/00* (2006.01)

(52) U.S. Cl. .................. 523/116; 523/115; 523/118

(58) Field of Classification Search .............. 523/113, 523/115, 116, 118
See application file for complete search history.

(56) References Cited

U.S. PATENT DOCUMENTS

| | | | |
|---|---|---|---|
| 3,367,992 A | 2/1968 | Bearden | |
| 4,338,242 A | 7/1982 | Burton | |
| 4,883,899 A | 11/1989 | Muramoto et al. | |
| 5,362,826 A | 11/1994 | Berge et al. | |
| 5,418,301 A * | 5/1995 | Hult et al. | 525/437 |
| 5,834,118 A * | 11/1998 | Rånby et al. | 428/482 |
| 6,316,519 B1 * | 11/2001 | Berge et al. | 522/182 |
| 6,787,629 B2 * | 9/2004 | Jia et al. | 528/196 |
| 7,241,856 B2 * | 7/2007 | Jin et al. | 528/301 |
| 2001/0012861 A1 * | 8/2001 | Liu | 523/118 |
| 2002/0086915 A1 * | 7/2002 | Montgomery | 523/115 |
| 2003/0032693 A1 * | 2/2003 | Angeletakis et al. | 523/116 |
| 2003/0161961 A1 * | 8/2003 | Barsotti et al. | 427/385.5 |
| 2004/0097627 A1 * | 5/2004 | Vallittu et al. | 524/430 |
| 2005/0124762 A1 * | 6/2005 | Cohen et al. | 525/191 |
| 2006/0047140 A1 * | 3/2006 | Hayakawa et al. | 560/217 |
| 2006/0058416 A1 * | 3/2006 | Brandenburg et al. | 523/116 |
| 2006/0258770 A1 * | 11/2006 | Anton et al. | 523/115 |

FOREIGN PATENT DOCUMENTS

| WO | WO 00/77070 | 12/2000 |
|---|---|---|
| WO | WO 01/46296 | 6/2001 |

OTHER PUBLICATIONS

Kawaguchi et al. Effect of Monomer Structure on the Mechanical Properties of Light-cured Composite Resins; Dent. Mater. J. 1989, 8, 40-45. Japanese Society for Dental Materials and Devices.*
Kawaguchi et al. Effect of Monomer Structure on the Mechanical Properties of Light-cured Unfilled Resins; Dent. Mater. J. 1988, 7, 174-181. Japanese Society for Dental Materials and Devices.*
C. M. Chung et al., "Development of a new photocurable composite resin with reduced curing shrinkage", Dental Materials 18 (2002) 174-178.
Qichun Wan et al., "Hyperbranched multi-methacrylates: their application in dental resin systems", Polymer Preprints 2000, 41(1), 155-156.
J. Macromol. Sci. Pure Appl. Chem. (2002) A39(4), 251-265.
J. Biomed. Mater. Res. (2002), 62(4), 622-627.
Biomaterials (2003), 24(1), 3845-3851.
Culbertson et al., J. Macromol. Sci. Pure Appl. Chem. (2000), A37(11), 1301-1315.
Macromolecules (1996), 29, 7717.
Dental Materials (1990), 6(4), 241-249.
Culbertson, J. Macromol. Sci. Pure Appl. Chem. (2002), A39(4), 267-286.

* cited by examiner

*Primary Examiner*—Mark Eashoo
*Assistant Examiner*—Michael Pepitone

(57) ABSTRACT

This invention relates to composite materials for restorative dentistry. More particularly, it relates to new components for dental composites, which impart an attractive combination of good mechanical properties and low shrinkage.

4 Claims, No Drawings

MATERIALS LEADING TO IMPROVED DENTAL COMPOSITES AND DENTAL COMPOSITES MADE THEREFROM

CROSS-REFERENCE TO RELATED APPLICATION

This application claims priority under 35 U.S.C. §119 from U.S. Provisional Application No. 60/609,588, filed Sep. 14, 2004.

FIELD OF THE INVENTION

This invention relates to composite materials for restorative dentistry. More particularly, it relates to new components for dental composites that impart an attractive combination of good mechanical properties and low shrinkage.

BACKGROUND OF THE INVENTION

In recent years, composite materials comprising highly filled polymers have become commonly used for dental restorations. Current composite materials contain crosslinking acrylates or methacrylates, inorganic fillers such as glass or quartz, and a photoinitiator system suitable for curing by visible light. Typical methacrylate materials include 2,2'-bis[4-(2-hydroxy-3-methacryloyloxypropyl)phenyl]propane ("Bis-GMA"); ethoxylated Bisphenol A dimethacrylate ("EBPDMA"); 1,6-bis-[2-methacryloyloxyethoxycarbonylamino]-2,4,4-trimethylhexane ("UDMA"); dodecanediol dimethacrylate ("D$_3$MA"); and triethyleneglycol dimethacrylate ("TEGDMA"). The structural formulae for these are shown below.

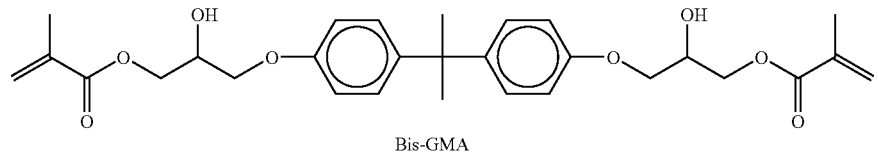
Bis-GMA

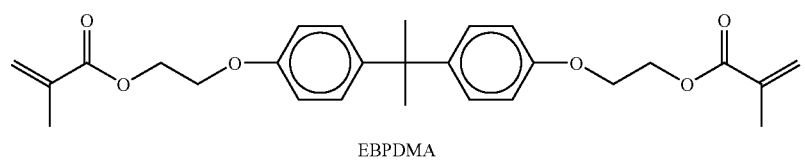
EBPDMA

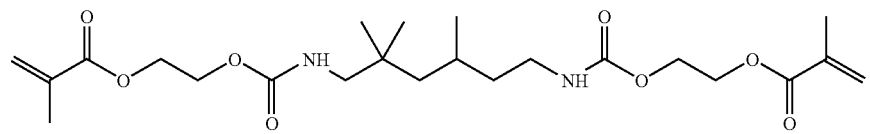
UDMA

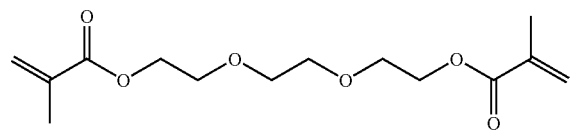
TEGDMA

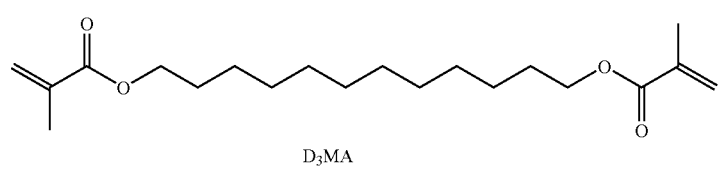
D$_3$MA

Dental composite materials offer a distinct cosmetic advantage over traditional metal amalgam. However, they do not offer the longevity of amalgam in dental fillings. The primary reasons for failure are excessive shrinkage during photopolymerization in the tooth cavity, which causes leakage and bacterial reentry. Another reason is they have inadequate strength and toughness, as reflected in the measured properties of flexural strength and fracture toughness. Hence, there is still a need for new monomers and new monomer combinations which, when polymerized, impart high fracture toughness and flexural strength in the resulting composite. It is also highly desirable to have low shrinkage and low shrinkage stress on polymerization.

One of the more common commercially used monomer is Bis-GMA, making it an especially important monomer in dental composites. However, it is highly viscous at room temperature and is insufficiently converted to polymer when cured. It is therefore diluted with a second, lower viscosity polymerizable component, typically an acrylate or methacrylate monomer, such as trimethylol propyl trimethacrylate, 1,6-hexanediol dimethacrylate, 1,3-butanediol dimethacrylate, ethylene glycol dimethacrylate, diethylene glycol dimethacrylate, TEGDMA, or tetraethylene glycol dimethacrylate. However, while providing low viscosity, lower viscosity components (generally low molecular weight monomers) contribute to increased shrinkage. Increasingly, Bis-GMA and TEGDMA have been combined with UDMA and EBPDMA, but shrinkage remains high enough that improvement is desirable.

In the search for superior dental composites, many research groups have looked to new monomers. For example, Culbertson describes the synthesis of trimethacrylate dental monomers derived from 1,1,1-tris(4-hydroxyphenyl)ethane (THPE). Culbertson treats THPE with ethylene or propylene carbonate, then caps the hydroxyl group with methacrylic anhydride:

The resulting compounds, 1,1,1-tri[4-methacryloxyethoxy)-phenyl]ethane ("THPE EO MA") when R=H and 1,1,1-tri[4-2-methyl-2-methacryloxyethoxy)-phenyl]ethane ("THPE PO MA") when R=methyl, are tested in dental composites. A 70/30 THPE PO MA/TEGDMA composite (TM7T3) has a shrinkage of 2.48%, while a 70/30 Bis-GMA/TEGDMA composite (Control 2) has a shrinkage of 3.28%. However, the flexural strength (113 MPa) is not improved over Control 2 (112.7 MPa). See *J. Macromol. Sci. Pure Appl. Chem.* (2002), A39(4), 251-265.

Chung et al. describe the synthesis and polymerization of trifunctional 20 methacrylates derived from 1,1,1-tris(4-hydroxyphenyl)ethane triglycidyl ether ("THPE GE") and their application as dental monomers. They are formed by treating THPE GE with methacrylic acid and then optionally acetylating the hydroxyl group. A disadvantage of these monomers is their high viscosity as compared with that of Bis-GMA. For example the product below (R=H) has a viscosity of 3510 Pa.s at 25° C. The acetylated compound (R=Ac) has a viscosity of 2810 Pa.s at 25° C. In comparison to Bis-GMA, whose viscosity is 54.7 Pa.s at 25° C., these monomers are much more viscous, which may limit their use in some composite formulations.

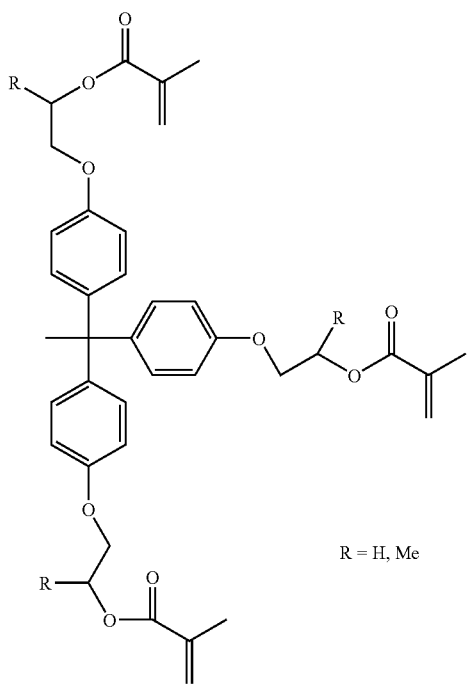

R = H, Me

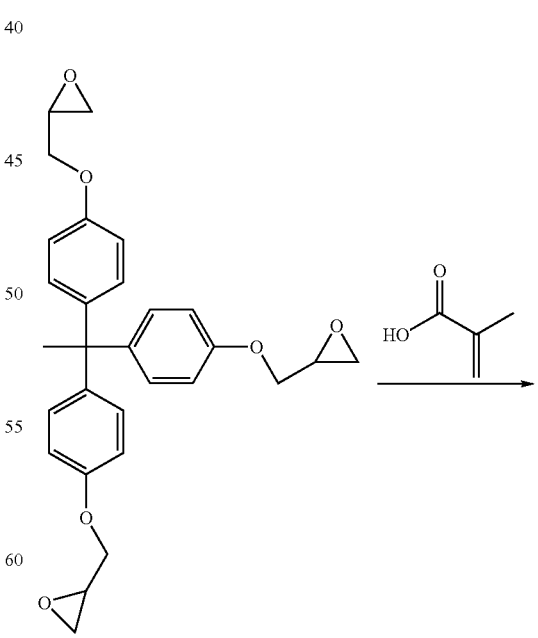

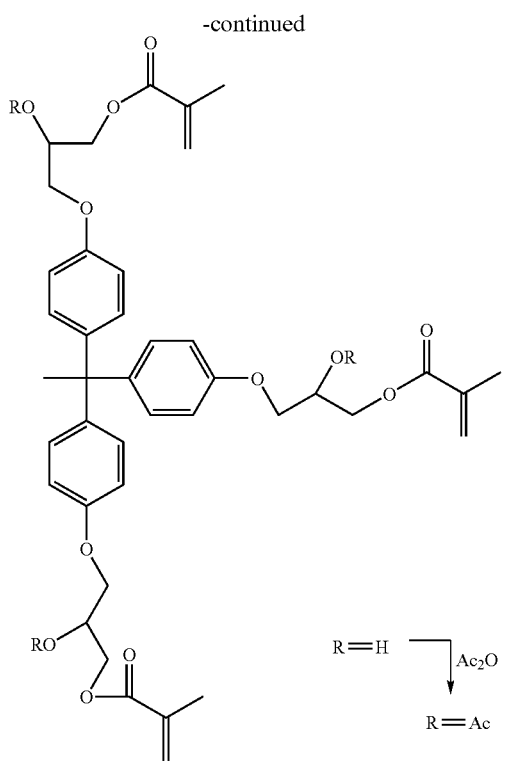

See *J. Biomed. Mater. Res.* (2002), 62(4), 622-627 and *Biomaterials* (2003), 24(1), 3845-3851.

Branched polyester methacrylates are another class of new dental monomers. For example, Culbertson, et al. used a variety of synthetic routes to methacrylate Boltorn H30, a commercially available polyester polyol with a dendritic structure (Perstorp AB, Perstorp, Sweden) that is synthesized by a condensation reaction of a pentaerythritol core with 2,2-dimethylolpropionic acid. The methacrylated Boltorn H30 was intended as a replacement for at least some of the Bis-GMA in dental composite materials. Culbertson, et al. evaluated the resulting partially and fully methacrylated materials as dental composite material components by mixing them in varying proportions with a 50:50 mixture of Bis-GMA and TEGDMA or with TEGDMA without Bis-GMA, and photopolymerizing the mixture. Resins made from a 50:50 mixture of methacrylated Boltorn H30 and TEGDMA had lower linear polymerization shrinkage than the 50:50 Bis-GMA/TEGDMA control. However, compressive strength and flexural strength were typically lower than the control. Since no filler was present, it is difficult to use these results to predict how such materials would perform in actual dental composite materials. See Culbertson et al., *J. Macromol. Sci. Pure Appl. Chem.* (2000), A37(11), 1301-1315.

Another class of materials is macromonomers (see definition below) with olefinic end groups. These are described by, for example, *Macromolecules* (1996), 29, 7717. These materials are usually prepared by polymerization of methacrylate monomers in the presence of a "catalytic chain transfer" (CCT) catalyst. The catalyst is typically a chelated cobalt species. Macromonomers have been described for use in automotive coatings, but not for dental composite applications.

There remains a need for dental composite materials that combine reduced shrinkage with sufficiently low viscosity, high polymerization rate, and acceptable mechanical properties.

SUMMARY OF THE INVENTION

In its first aspect, the present invention is a compound having the Formula I:

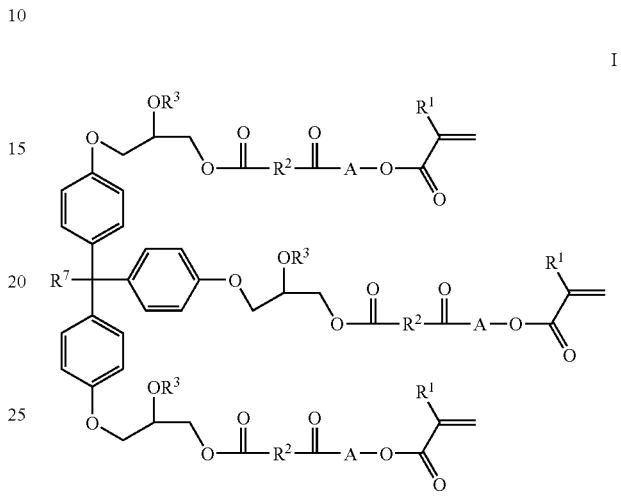

wherein
each $R^1$ is independently hydrogen or methyl;
each $R^2$ is an alkylene having 2 to 14 carbon atoms, or an alkenylene having 2 to 8 carbon atoms, or a divalent alicyclic hydrocarbon having 5 to 14 carbon atoms, or a phenylene, which is optionally substituted with halogen or an alkyl group having 1 to 5 carbon atoms;
each $R^3$ is independently selected from hydrogen, acetyl, methyl, ethyl, $C_{3-6}$ linear or branched alkyl, or benzyl;
each $R^7$ is independently selected from hydrogen, methyl, ethyl, $C_{3-6}$ linear or branched alkyl, phenyl, or benzyl;
and A is a repeat unit of the formula:

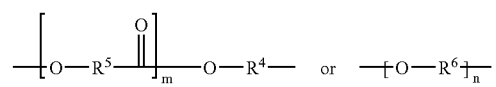

wherein:
each $R^4$ is independently an alkylene having 2 or 3 carbon atoms,
each $R^5$ is independently an alkylene having 2 to 7 carbon atoms,
each $R^6$ is independently an alkylene having 2 to 5 carbon atoms,
m is an integer of 1 to 10,
and n is an integer of 1 to 10.

In its second aspect, the present invention is a new (meth)acrylated hyperbranched polyester polyol that is suitable for use in dental composite materials.

In its third aspect, the present invention is an uncured dental composite material incorporating the compound of Formula I and the new (meth)acrylated hyperbranched polyester polyol.

In its fourth aspect, the present invention is an uncured dental composite material incorporating a compound of the Formula IV

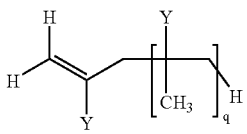

IV wherein:
q is 1 to 20, and
each Y is —COOR$^{17}$, where
each R$^{17}$ is independently selected from the group consisting of hydrogen, substituted or unsubstituted straight, branched, or cyclic alkyl having 1 to 20 carbon atoms, aryl, benzyl, and
—(CH$_2$)$_n$Si(OCH$_3$)$_3$ wherein n is 2 to 5.

In its fifth aspect, the present invention is an uncured dental composite material incorporating a compound of the Formula V

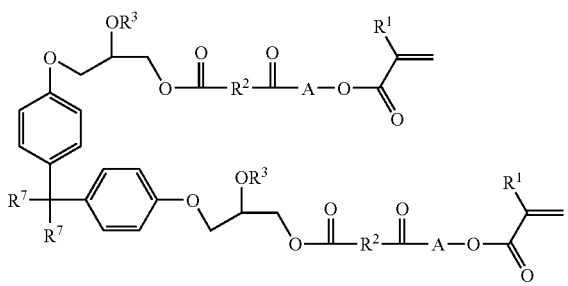

V wherein:
each R$^1$ is independently hydrogen or methyl;
each R$^2$ is an alkylene having 2 to 14 carbon atoms, or an alkenylene having 2 to 8 carbon atoms, or a divalent alicyclic hydrocarbon having 5 to 14 carbon atoms, or a phenylene, which is optionally substituted with halogen or an alkyl group having 1 to 5 carbon atoms;
each R$^3$ is independently selected from hydrogen, acetyl, methyl, ethyl, C$_{3-6}$ linear or branched alkyl, or benzyl;
each R$^7$ is independently selected from the group consisting of hydrogen, methyl, ethyl, C$_{3-6}$ linear or branched alkyl, phenyl, or benzyl, and the two R$^7$ groups may be taken together to form a substituted or unsubstituted cyclic aliphatic ring having 5 or 6 carbons therein, including the carbon to which both R$^7$ groups are attached.
each A is a repeat unit of the formula:

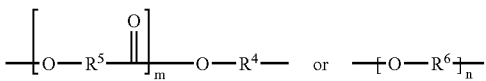

wherein:
each R$^4$ is independently an alkylene having 2 or 3 carbon atoms,
each R$^5$ is independently an alkylene having 2 to 7 carbon atoms,
each R$^6$ is independently an alkylene having 2 to 5 carbon atoms,
m is an integer of 1 to 10, and
n is an integer of 1 to 10.

DETAILED DESCRIPTION OF THE INVENTION

In the context of this application, a number of terms are utilized.

The term "dental composite material" as used herein denotes a composition that can be used to remedy natural or induced imperfections in, or relating to, teeth. Examples of such materials are filling materials, reconstructive materials, restorative materials, crown and bridge materials, inlays, onlays, laminate veneers, dental adhesives, teeth, facings, pit and fissure sealants, cements, denture base and denture reline materials, orthodontic splint materials, and adhesives for orthodontic appliances. The term "uncured dental composite material" specifically refers to such material before it is subjected to curing processes.

"Dendrimers" are macromolecules having a highly regular tree-like structure. "Hyperbranched" polymers resemble dendrimers, but are less regularly structured. As used herein, the term "hyperbranched polymer" refers to both dendrimers and such less regularly structured polymers.

The term "macromonomer" as used herein means an oligomer of limited chain length or molecular weight that contains at least one terminal olefinic moiety.

As used herein, the term "alkyl" means a univalent group derived from an alkane by removing a hydrogen atom from any carbon atom: —C$_n$H$_{2n+1}$ where n≥1.

As used herein, the term "hydrocarbyl", when used in relation to a radical, denotes a univalent radical containing only carbon and hydrogen.

As used herein, the term "hydrocarbyl moiety" denotes a chemical group that contains only carbon and hydrogen and may be able to form more than one single covalent bond; the term may encompass straight chain, branched chain, cyclic, aromatic species, and structures combining combinations of the foregoing.

As used herein, the term "alkylene" means the divalent radical derived from an alkane by removing a hydrogen atom from each of two different carbon atoms: —C$_n$H$_{2n}$— where n>1.

As used herein, the term "alkenylene" means a straight or branched chain alkenediyl containing one olefinic bond in the chain, e.g. —CH=CH— (ethenylene), —CH$_2$CH=CH— (propenylene), etc.

As used herein, "an alicyclic group" means a non-aromatic hydrocarbon group containing a cyclic structure therein.

As used herein, the term "benzyl" refers to the C$_6$H$_5$CH$_2$— radical.

As used herein, the term "phenyl" refers to the C$_6$H$_5$— radical.

As used herein, the term "phenylene" refers to the divalent radical, —C$_6$H$_4$—.

As used herein, the term "aryl" means a univalent group whose free bonding site is to a carbon atom of an aromatic ring. An example is the "phenyl" group.

As used herein, "hydroxy carboxylic acid" means an organic compound containing both —COOH and hydroxyl groups.

As used herein, the term "carboxy methacrylate" means a compound containing a carboxylic acid and a methacrylate group.

As used herein, the terms "(meth)acrylic" and "(meth) acrylate" refer to both methacrylic and acrylic and to methacrylate and acrylate, respectively.

As used herein, the term "polymerizable (meth)acrylic ester component" means one or more materials that bear (meth)acrylate groups, such that the materials are capable of undergoing free radical polymerization.

As used herein, the term "polyol" means an organic compound having more than one hydroxyl (—OH) group per molecule.

As used herein, the term "caprolactone" means ε-caprolactone, CAS Registry # 502-44-3:

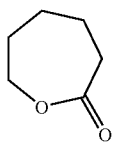

Where a range of numerical values is recited herein, unless otherwise stated, the range is intended to include the endpoints thereof, and all integers and fractions (provided the context allows) within the range.

Compound of Formula I

The present invention provides a compound of the Formula I, as shown below.

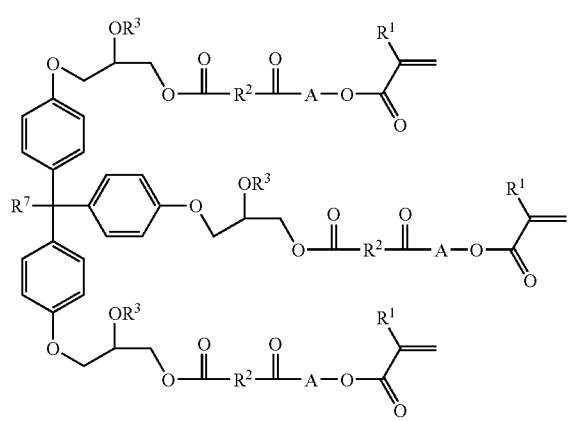

I wherein:

each $R^1$ is independently hydrogen or methyl;

$R^2$ is an alkylene having 2 to 14 carbon atoms, or an alkenylene having 2 to 8 carbon atoms, or a divalent alicyclic hydrocarbon having 5 to 14 carbon atoms, or a phenylene that is optionally substituted with halogen or an alkyl group having 1 to 5 carbon atoms;

each $R^3$ is independently selected from the group consisting of hydrogen, acetyl, methyl, ethyl, $C_{3-6}$ linear or branched alkyl, and benzyl;

$R^7$ is selected from the group consisting of hydrogen, methyl, ethyl, $C_{3-6}$ linear or branched alkyl, phenyl, and benzyl; and A is a repeat unit of the formula:

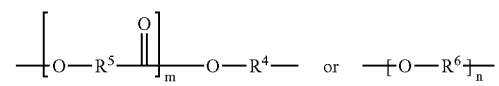

wherein:

each $R^4$ is independently an alkylene having 2 or 3 carbon atoms;

each $R^5$ is independently an alkylene having 2 to 7 carbon atoms;

each $R^6$ is independently an alkylene having 2 to 5 carbon atoms atoms;

m is an integer of 1 to 10; and n is an integer of 1 to 10.

The preferred structure is one in which
each $R^1$ is methyl;
each $R^2$ is —(CH$_2$CH$_2$)—;
each $R^3$ is H;
$R^7$ is methyl; and
A is:

—O—R$^6$— wherein:

$R^6$ is —(CH$_2$CH$_2$)—.

A preferred compound of Formula I is shown below.

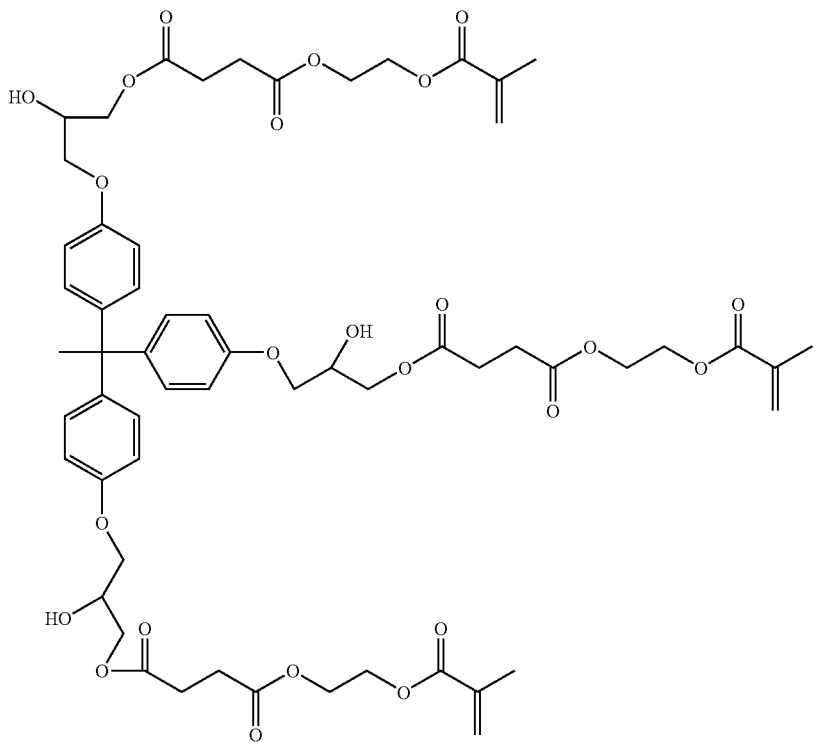

One method of preparing the compound of Formula I is the following:

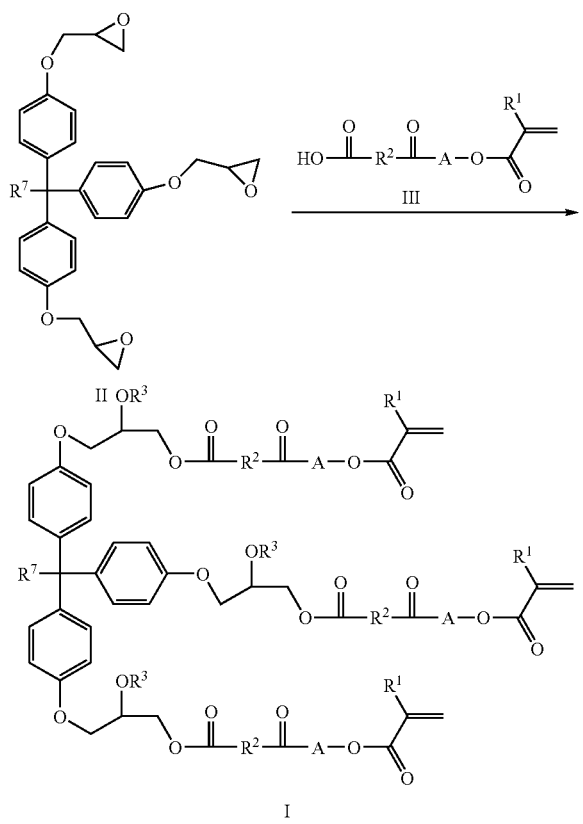

Triepoxides of formula II are commercially available. For example, compound II where $R^7$=methyl (i.e., 1,1,1-tris(p-hydroxyphenylethane)triglycidyl ether), is available from E. I. du Pont de Nemours & Co., Inc. (Wilmington, Del.) under the trade name THPE-GE. It can be prepared by treatment of 1,1,1-tris(p-hydroxyphenylethane) with epichlorohydrin.

Other compounds of formula II (where $R^7$ is defined as above) can be prepared by the scheme below.

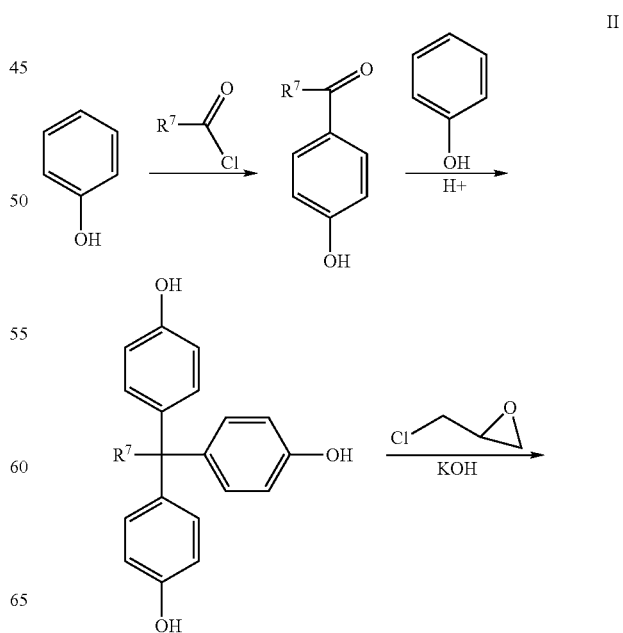

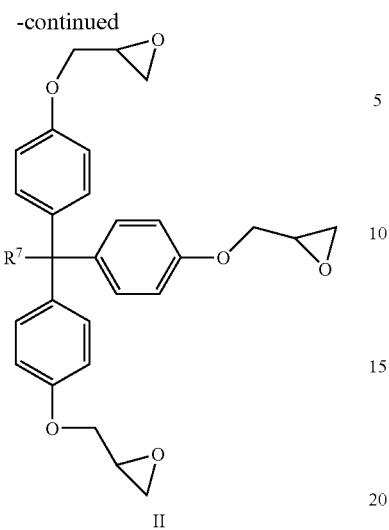

A compound of formula II is treated with at least three moles of the carboxy methacrylate compound of formula III. The carboxylic acid of formula III opens the epoxide rings in formula II to give the desired product. The reaction gives the hydroxy compound ($R^3$=H). The hydroxy compound can be further alkylated or acylated by any means known in the art. For example, it can be treated with acetic anhydride to give the acetylated product ($R^3$=—C(O)CH$_3$).

Suitable carboxy methacrylate compounds can be prepared by treatment of, for example, hydroxyethyl(meth)acrylate or hydroxypropyl(meth)acrylate with a cyclic anhydride to give the corresponding carboxy methacrylate compound. Suitable anhydrides include succinic anyhydride, maleic anhydride, and phthalic anhydride. Other suitable anhydrides include, for example, the following:

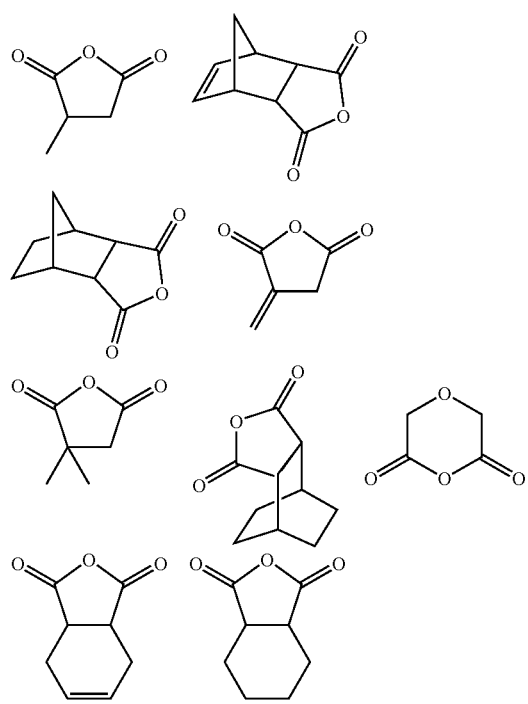

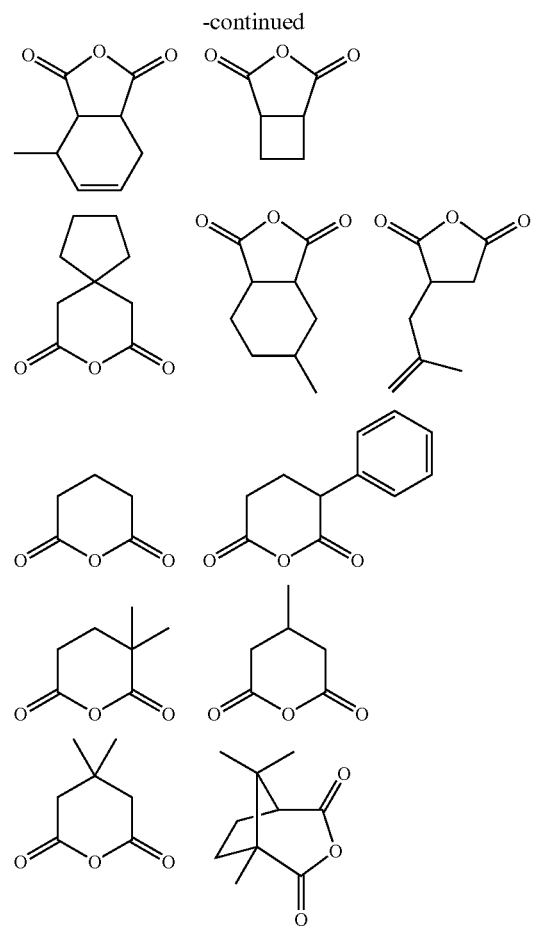

Some examples of syntheses and structures of carboxy methacrylates (IIIA, IIIB, IIIC) are shown below.

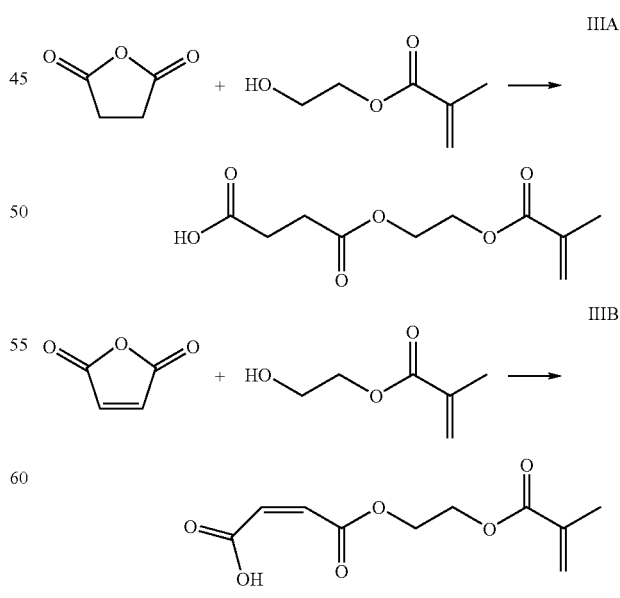

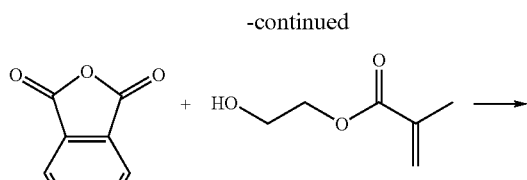 

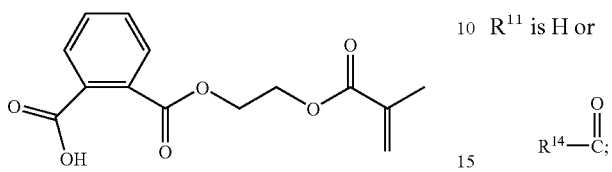

Other suitable carboxy methacrylates are described in U.S. Pat. No. 4,883,899, Col 2, line 37 to Col 3, line 17. There, hydroxyethyl methacrylate is used as an initiator for the ring opening polymerization of caprolactone. The resulting hydroxy methacrylates are commercially available from Daicel Chemical Industries, Ltd. (Tokyo, Japan) under the trade name Placcel. For example, Placcel FM 3 is the addition product of hydroxyethyl methacrylate with three moles of caprolactone. These products can be reacted with cyclic anhydrides to give carboxy functional methacrylates useful in the present invention.

Catalysts for the reaction may include any known in the art for the reaction of carboxylic acids with epoxides. They may include nitrogen-containing compounds such as triethylamine, imidazole, 2-methyl imidazole, N,N-dimethyl benzyl amine, pyridine, and the like. They may include Lewis acids such as zinc acetate or zinc stearate.

(Meth)acrylated Hyperbranched Polyester Polyols

The present invention also provides new (meth)acrylated hyperbranched polyester polyols that are suitable for use in dental composite materials. These are produced by a process of (1) preparing a hyperbranched polyester polyol, and (2) converting all or part of the terminal hydroxyl groups of the hyperbranched polyester polyol to (meth)acrylate groups.

The hyperbranched polyester polyols can be produced by heating a mixture that includes:

(i) one or more hyperbranching monomers having the formula:

$(R^8O)_n R^9 (C(O)OR^{10})_m$ each of the ($R^8O$) groups is bonded to $R^9$ through the oxygen of the $R^8O$ group, and each of the ($C(O)OR^{10}$) groups is bonded to $R^9$ through the carbon of the $C(O)$ group.]

(ii) one or more chain extenders selected from the group consisting of a hyroxy carboxylic acid, a lactone of a hydroxy carboxylic acid, a linear ester of a hydroxyl carboxylic acid, and a combination thereof, said hydroxy carboxylic acid and linear ester having the structural formula:

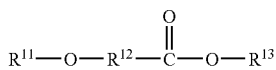

wherein:

each $R^8$ is independently H or

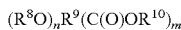

$R^{11}$ is H or

$R^9$ is a $C_{1-12}$ hydrocarbyl moiety capable of forming m+n single covalent bonds;

$R^{10}$ is H or a $C_{1-12}$ hydrocarbyl radical;

$R^{12}$ is a $C_{1-12}$ hydrocarbyl moiety capable of forming two single covalent single bonds;

$R^{13}$ is H or a $C_{1-12}$ hydrocarbyl radical;

$R^{14}$ is H or a $C_{1-10}$ hydrocarbyl radical;

n+m ranges from 3 to 6, and either n or m must be 1; and, optionally, (iii) a molecular weight controlling agent having the formula:

$R^{15}\text{-}Z_k,$ wherein:

$R^{15}$ is a $C_{1-10}$ hydrocarbyl moiety capable of forming from 1 to 6 single covalent bonds;

Z is a hydroxyl, carboxyl, amine or epoxy group; and k ranges from 1 to 6 and is equal to the number of covalent bonds capable of being formed on $R^{15}$.

Suitable hyperbranching monomers include those having one carboxyl group and two hydroxyl groups, two carboxyl groups and one hydroxyl group, one carboxyl group and three hydroxyl groups, or three carboxyl groups and one hydroxyl group. Some of the suitable hyperbranching monomers include dialkylol propionic acid, such as dimethylolpropionic acid (DMP) and diethylolpropionic acid; trimethylolacetic acid; citric acid; malic acid; and a combination thereof. DMP is the preferred hyperbranching monomer for use in the present invention.

The chain extender is selected from the group consisting of a hydroxy carboxylic acid, a lactone of a hydroxy carboxylic acid, a linear ester of a hydroxy carboxylic acid, and a combination thereof.

Some of the suitable hydroxy carboxylic acids include glycolic acid; lactic acid; and 3-hydroxy carboxylic acids, e.g., 3-hydroxypropionic acid, 3-hydroxybutyric acid, 3-hydroxyvaleric acid, and hydroxypivalic acid.

Some of the suitable lactones include caprolactone; 6-valerolactone; and lactones of hydroxy carboxylic acids, such as, glycolic acid; lactic acid; and 3-hydroxy carboxylic acids, such as, 3-hydroxypropionic acid, 3-hydroxybutyric acid, 3-hydroxyvaleric acid, and hydroxypivalic acid. Caprolactone is the preferred chain extender for use in the present invention.

The weight ratio of the hyperbranching monomer to the chain extender in the mixture ranges from 1/0.3 to 1/20, preferably from 1/1 to 1/10 and more preferably from 1/1.5 to 1/4.

The mixture can further include one or more molecular weight controlling agents having in the range of 1 to 6 functionalities selected from the group consisting of hydroxyl, amine, epoxide, carboxyl and a combination thereof. Some of the suitable molecular weight controlling agents can include polyhydric alcohols, such as ethylene glycol, propanediols, butanediols, hexanediols, neopentylglycol, diethylene glycol, cyclohexanediol, cyclohexanedimethanol, trimethylpentanediol, ethylbutylpropanediol, ditrimethylolpropane, trimethylolethane, trimethylolpropane, glycerol, pentaerythritol, dipentaerythritol; polyalkylene glycol, such as, polyethylene glycol and polypropylene glycol. Monohydric alcohols can be also used, such as, cyclohexanol and 2-ethylhexanol. The preferred polyhydric alcohols are ditrimethylolpropane, trimethylolethane, trimethylolpropane and pentaerythritol. Pentaerythritol is a particularly preferred molecular weight controlling agent for use in the present invention.

The preferred hyperbranched polyester polyols for use in the present invention involve the reaction of caprolactone, DMP, and pentaerythritol.

The highly branched polyester polyols can be produced by heating (to induce polymerization), in one step, the mixture that includes the chain extender and the hyperbranching monomer. If desired, the mixture in the foregoing one-step polymerization process can also include the molecular weight controlling agent.

A modification of the foregoing process is to produce the hyperbranched polyester polyol in two stages. The first stage involves heating the molecular weight controlling agent, the hyperbranching monomer, and only a portion of chain extender to produce an intermediate product, followed by heating the intermediate product with the remainder of the chain extender. Typically, the process involves using from 10 to 90, preferably 20 to 60 and more preferably 30 to 40 weight percent of the chain extender in the first stage, the remainder of the chain extender being used during the second stage.

The hyperbranched polyester polyols produced by the processes described above can be prepared by a batch process or by a continuous polymerization process. Generally, the processes for forming the hyperbranched polyester polyol take place at reaction temperatures in the range of from 60° C. to 200° C. and preferably, in the range of from 80° C. to 170° C., with typical reaction times ranging from 1 hour to 24 hours, preferably 1 hour to 4 hours. The polymerization can be catalyzed by conventional polyester polymerization catalysts, as described below.

The hyperbranched polyester polyol reaction product to be used in the present invention preferably has a number average molecular weight not exceeding 30,000, preferably in the range of from 1,000 to 30,000, more preferably in the range of 2,000 to 20,000, most preferably in the range of 5,000 to 15,000. The Tg (glass transition temperature measured at 10° C./min. heating rate) of the hyperbranched polyester polyol reaction product preferably ranges from −70° C. to 50° C., preferably from −65° C. to 40° C., and more preferably from −60° C. to 30° C.

The hyperbranched polyester polyol is then combined and optionally heated with one or more end capping agents having the formula $X-R^{16}$ wherein $R^{16}$ is a $C_{1-12}$ hydrocarbyl radical and X is a carboxylic acid, carboxylic ester, carboxylic halide, or epoxy group, or having the formula $R^{16}-X-R^{16}$ wherein $R^{16}$ is a $C_{1-12}$ hydrocarbyl radical and X is a carboxylic anhydride group, provided that the resulting degree of end capping is at least 25%, with radically polymerizable end groups constituting at least 25% of all end groups. The degree of capping with radically polymerizable end groups can be determined by a combination of $^1H$ NMR, $^{13}C$ NMR and two-dimensional NMR spectroscopy.

The conversion of hydroxyl groups to (meth)acrylate groups may be carried out according to any method known in the art. Preferred end capping agents are methacrylic acid, methacrylic anhydride, and methacryloyl chloride. Another option is to methacrylate only a portion of the hydroxyl groups and then treat the remaining hydroxyl groups with another reagent that is not capable of participating in free radical polymerization when the uncured dental composite is cured. For example, a portion of the hydroxyl groups can be capped with methacrylic anhydride, and the remaining hydroxyl groups can be capped with acetic anhydride.

Expressed in greater detail, a preferred (meth)acrylated hyperbranched polyester polyol can be made by a process comprising the steps of:

(a) combining caprolactone, pentaerythritol, dimethylolpropionic acid, at least one aromatic solvent, and a polyester polymerization catalyst;

(b) heating the product of step (a) to a temperature between about 170° C. and 200° C. for a time sufficient to achieve an acid number (see analytical section, below) of no greater than about 3.5;

(c) cooling the product of step (b) to about 130° C.;

(d) optionally, adding to the product of step (c) additional caprolactone while maintaining the temperature at about 130° C.;

(e) maintaining the temperature of the product of step (d) at about 130° C. for 2 to 4 hours until a Gardner-Holdt viscosity [ASTM D1545 "Standard Test Method for Viscosity of Transparent Liquids by Bubble Time Method"] of Z to Z2 (approximately 0.023 to 0.036 Pascal—Seconds) is achieved;

(f) cooling the product of step (e) to 80° C. or lower;

(g) adding to the product of step (f) at least one member of the group consisting of methacrylic acid, methacrylic anhydride, methacryloyl chloride, optionally in the presence of an aprotic organic solvent, while mixing at a temperature between about 23° C. and about 100° C.; and (h) isolating the reaction product of step (g).

Some aromatic solvents suitable for step (a) are toluene, benzene, p-xylene, m-xylene, o-xylene, and mixtures thereof.

Typical polyester polymerization catalysts that are useful in step (a) include, but are not limited to, $Sn(2\text{-ethylhexanoate})_2$, $Sn(n\text{-octanoate})_2$; p-toluenesulfonic acid; and methanesulfonic acid. Tin(II) catalysts are preferred.

Some aprotic organic solvents for suitable for step (g) are tetrahydrofuran ("THF"), diethyl ether, pyridine, N,N-dimethylacetamide, N,N-dimethylformamide, dimethyl sulfoxide, N-methylpyrrolidone, $CH_2Cl_2$, $CHCl_3$, chlorobenzene, o-dichlorobenzene, benzene, toluene, xylene, and mixtures thereof.

The reaction product is typically isolated in step (h) by either of two methods. The first method involves an aqueous workup. The organic phase is typically washed with an aqueous basic solution, such as saturated $NaHCO_3$ (aq), to remove acidic impurities. It may optionally be washed with dilute aqueous acidic solution (e.g., 10% HCl) to remove basic impurities such as pyridine. Then it is washed with saturated NaCl solution to remove the bulk of the water. It is optionally dried with a drying agent, such as $MgSO_4$, to remove final traces of water. Then the organic solvent is removed, optionally under vacuum, to obtain the final product. A second method for isolating the product is to perform a high vacuum distillation directly on the reaction mixture. This is typically done at 0.5 torr (66 Pa) to distill off methacrylic acid and unreacted methacrylic anhydride. The second method typically is not used when methacryloyl chloride is used as the capping agent.

may have to be determined experimentally. Generally speaking, however, a good balance of properties should be obtained when the material of Formula I is used at about 70 weight percent, based on the total weight of the (meth)acrylic ester component present in the composite material.

A particularly preferred uncured dental composite according to the present invention comprises a compound of Formula I as follows:

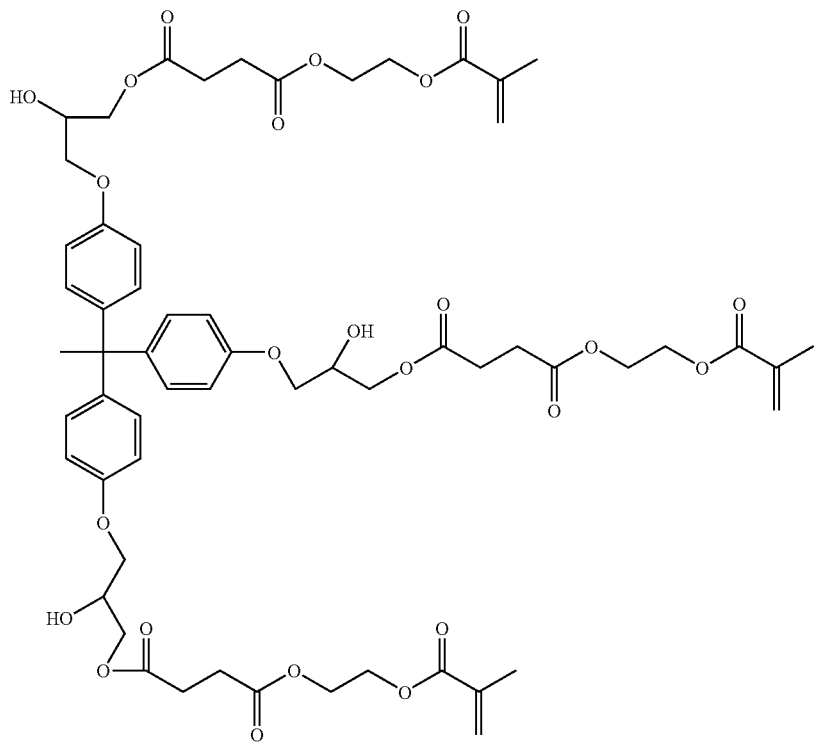

Dental Composite Materials

The present invention further provides an uncured dental composite material comprising:
(a) at least one polymerizable (meth)acrylic ester component;
(b) at least one polymerization initiator compound; and
(c) at least one filler; provided that the uncured dental composite must include at least one of the following:
(1) at least one compound of Formula I;
(2) at least one (meth)acrylated hyperbranched polyester polyol of the present invention;
(3) at least one compound of Formula IV; and
(4) at least one compound of Formula V.

Polymerizable (Meth)Acrylic Ester Component

The compound of Formula I, when present, could account for the entire (meth)acrylic ester content in the composite. However, this is not preferable because of its high viscosity. Therefore, it is preferred that the compound of Formula I be used in combination with another polymerizable (meth)acrylic ester component having a lower viscosity than that of the Formula I material. The relative amounts of the two materials will, of course, depend on the nature of the two materials. That ratio that provides the best overall balance of properties (shrinkage, flexural strength, and fracture toughness, etc.)

combined with a (meth)acrylated hyperbranched polyester polyol synthesized from the two-stage process described in detail above, namely combining and heating pentaerythritol, DMP, and a portion of caprolactone to form a first intermediate product, and then heating the first intermediate product with additional caprolactone to produce a second intermediate reaction product, followed by heating the second intermediate reaction product with methacrylic anhydride. In this preferred uncured dental composite, the compound of Formula I and the (meth)acrylated hyperbranched polyester polyol are used in a weight ratio of about 7/3. At this weight ratio, the high viscosity of the compound of Formula I is sufficiently reduced by the (meth)acrylated hyperbranched polyester polyol to allow fillers to be added and adequately mixed. The resulting material, when cured, shows relatively low shrinkage with good mechanical properties.

Unlike the high viscosity materials of Formula I, the (meth) acrylated hyperbranched polyester polyols of the present invention have sufficiently low viscosity to be used alone. However, the use of the latter materials as the sole polymerizable (meth)acrylic ester component, even with fillers, does not provide dental composites with a good balance of properties. Therefore, the (meth)acrylated hyperbranched polyester polyols of the present invention should be used in combination with a higher viscosity polymerizable (meth)acrylic ester component such as, but not limited to, Bis-GMA, THPE GE MA (defined above), THPE PO MA (defined above), or, preferably, the compound of Formula I. The relative amounts of the two materials will, of course, depend on the nature of the two materials. That ratio that provides the best overall balance of properties (shrinkage, flexural strength, and fracture toughness, etc.) may have to be determined experimentally.

The uncured dental composite can also comprise macromonomers that contain olefinic end groups. Particularly suitable macromonomers for use in the present invention are compounds of the Formula IV.

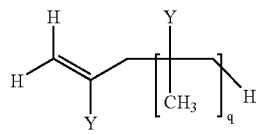

IV wherein:
q is 1 to 20, and
each Y is —COOR$^{17}$, where the R$^{17}$ of each Y is independently selected from the group consisting of hydrogen, substituted or unsubstituted straight, branched, or cyclic alkyl having 1 to 20 carbon atoms, aryl, benzyl, and —CH$_2$)$_n$Si(OCH$_3$)$_3$ wherein n is 2 to 5.

Suitable macromonomers are dimers, trimers, tetramers, or higher oligomers of methyl, ethyl, propyl, butyl, 2-ethylhexyl, decyl, cyclohexyl, benzyl, glycidyl, hydroxyethyl, or hydroxypropyl methacrylate, methacrylic acid, or methacryloxypropyltrimethoxysilane.

The preferred macromonomer is the compound of Formula IV in which R$^{17}$ is methyl, and q is 1.

Macromonomers are most easily made by a metal chelate catalytic chain transfer, for example, using a cobalt chelate, as described in U.S. Pat. No. 5,362,826, Col. 9, line 14 to Col. 9, line 57.

Preferred uncured dental composite of the present invention is one that comprises at least one compound of Formula I with at least one macromonomer of Formula IV. In general, the macromonomers of Formula IV act as a viscosity-lowering agent for the compound of Formula I. In addition, while not wishing to be bound by any theory, it is believed that the macromonomers of Formula IV function as chain transfer agents during the polymerization of the compounds of Formula I. More preferred are those compositions in which the compound of Formula I is

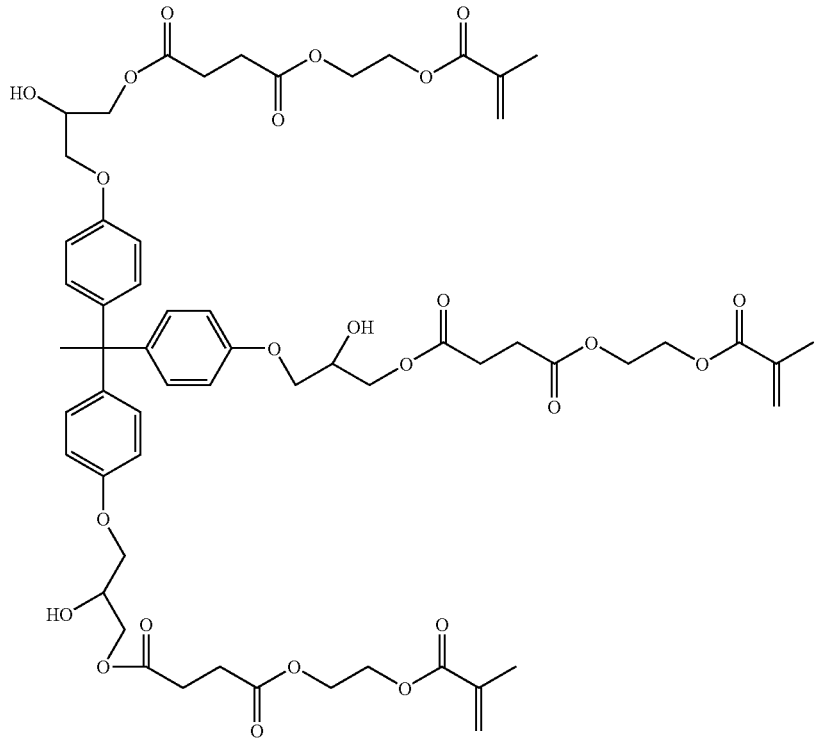

and the compound of Formula IV is

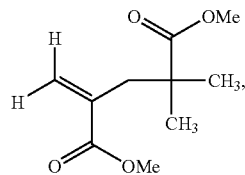

wherein the weight ratio of the preferred compound of Formula I to the preferred compound of Formula IV is 9/1. This ratio provides a workable, uncured composition (i.e., one that allows for the addition and mixing of fillers), which, upon curing, provides an extremely attractive balance of low shrinkage and excellent physical properties.

Another compound that may be used in addition to, or in place of, a compound of Formula I is a compound of Formula V.

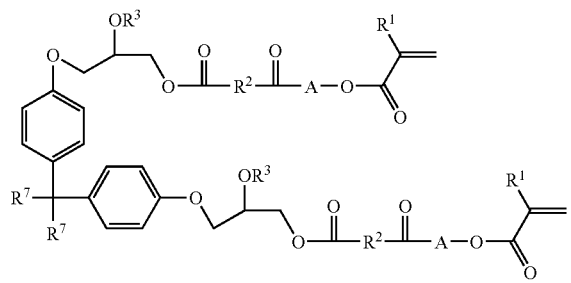

wherein $R^1$, A, $R^2$, $R^3$, are as defined in relation to the compound of Formula I, and each $R^7$ is independently selected from the group consisting of hydrogen, methyl, ethyl, $C_{3-6}$ linear or branched alkyl, phenyl, benzyl, and the two $R^7$ groups may be taken together to form a substituted or unsubstituted cyclic aliphatic ring having 5 or 6 carbons in the ring, including the carbon to which both $R^7$ groups are attached.

A preferred compound of Formula V is shown below.

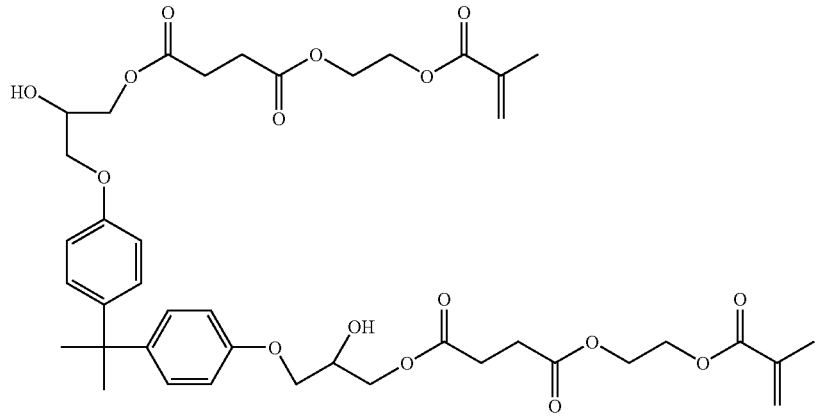

Such compounds may be synthesized as shown below.

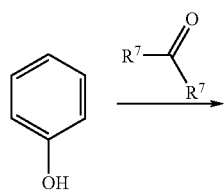

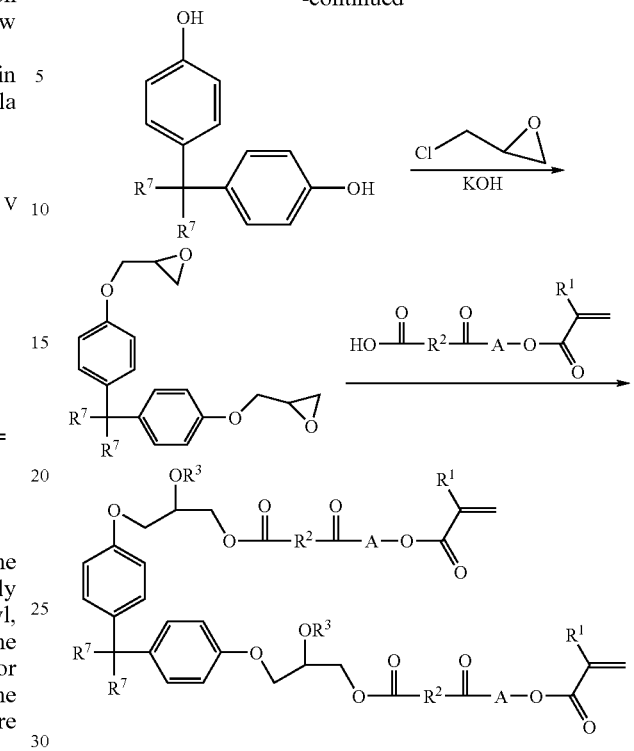

Some of the compounds of Formula V have been described in, for example, U.S. Pat. No. 3,367,992 Col. 6, line 27 to Col. 7, line 21, although not in relation to use in dental composites.

The polymerizable(meth)acrylic ester component may include, in addition to any of the following:

(1) at least one compound of Formula I;
(2) at least one (meth)acrylated hyperbranched polyester polyol of the present invention;
(3) at least one compound of Formula IV; and
(4) at least one compound of Formula V, additional polymerizable (meth)acrylic ester compounds. These additional polymerizable (meth)acrylic ester compounds may include both monofunctional compounds and polyfunctional compounds, where "monofunctional" denotes a compound having one (meth)acrylic group and "polyfunctional" denotes a compound having more than one (meth)acrylic ester group.

Specific examples of monofunctional (meth)acrylic ester compounds include methyl(meth)acrylate, ethyl(meth)acrylate, propyl(meth)acrylate, butyl(meth)acrylate, hydroxyethyl(meth)acrylate, benzyl(meth)acrylate, methoxyethyl (meth)acrylate, glycidyl(meth)acrylate, tetrahydrofurfuryl (meth)acrylate, and the hydroxyethyl(meth)acrylate monoester of trimellitic anhydride.

Specific examples of polyfunctional (meth)acrylic ester compounds include di(meth)acrylates of ethylene glycol derivatives as represented by the general formula

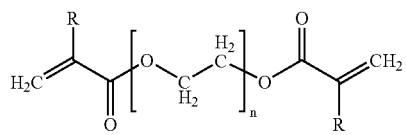

wherein R is hydrogen or methyl and n is an integer in a range of from 1 to 20, such as ethylene glycol di(meth)acrylate, diethylene glycol di(meth)acrylate, triethylene glycol di(meth)acrylate, and polyethylene glycol di(meth)acrylate.

Other examples of polyfunctional (meth)acrylic ester compounds include, without limitation, Bis-GMA, EBPDMA, UDMA, and other urethane di(meth)acrylates.

Polymerization Initiator Compounds

Suitable polymerization initiator compounds include peroxy-type initiators such as benzoyl peroxide, dicumyl peroxide, lauryl peroxide, tributyl hydroperoxide, and other materials familiar to those skilled in the art. The use of activators may be advantageous in some formulations. Suitable activators include, for example, N,N-bis-(hydroxyalkyl)-3,5-xylidines, N,N-bis-(hydroxyalkyl)-3,5-di-t-butylanilines, barbituric acids and their derivatives, and malonyl sulfamides.

Azo-type initiators such as 2,2'-azobis(isobutyronitrile), 2,2'-azobis(2,4-dimethyl valeronitrile), 2,2'-azobis(2-methyl butane nitrile), and 4,4'-azobis(4-cyanovaleric acid) may also be used.

Generally, photoinitiator systems include photosensitizers in combination with initiators. Suitable photosensitizers include, for example, camphorquinone, benzoin ethers, α-hydroxyalkylphenones, acylphosphine oxides, α,α-dialoxyacetophenones, α-aminoalkylphenones, acyl phosphine sulfides, bis acyl phosphine oxides, phenylglyoxylates, benzophenones, thioxanthones, metallocenes, bisimidazoles, and α-diketones. Photoinitiating initiators include, for example, ethyl dimethylaminobenzoate, dimethylaminoethyl methacrylate, dimethyl-p-toluidine, and dihydroxyethyl-p-toluidine.

Some materials are able to function as photoinitiators by themselves. Such materials include, for example, acylphosphine oxides.

Dental composites are typically cured with blue light in the 400-500 nm region. A preferred photosensitizer is camphorquinone, used in conjunction with a tertiary amine like ethyl dimethylaminobenzoate or dimethylaminoethyl methacrylate.

The polymerization initiator (optionally with a photosensitizer) can be used in the range of about 0.1 weight percent to about 5 weight percent, preferably about 0.2 weight percent to about 3 weight percent, and more preferably about 0.2 weight percent to about 2 weight percent. The percentages are based on the total weight of the uncured dental composite, exclusive of filler.

Fillers

One class of fillers that may be used in the uncured dental composites of the present invention is inorganic fillers. Among the preferred inorganic fillers are barium aluminum silicate, barium aluminum borosilicate, lithium aluminum silicate, strontium fluoride, lanthanum oxide, zirconium oxide, bismuth phosphate, calcium tungstate, barium tungstate, bismuth oxide, tantalum aluminosilicate glasses, and related materials. Glass beads, silica, quartz, borosilicates, alumina, alumina silicates, and other fillers may also be employed. Mixtures of inorganic fillers may also be employed. The mean particle size of the inorganic fillers is preferably between about 0.5 and 15 µm, more preferably between 0.5 and 5 µm, most preferably between 0.5 and 2 µm. Mean particles size may be determined, for example, by the use of a laser light diffraction particle size analyzer, such as those sold by Malvern Instruments, Malvern, U.K.

A first inorganic filler having a mean particle size between 0.5 and 15 µm can be combined with a second inorganic filler (of the same or different material) having a larger mean particle size in order to afford a workable composition with a total filler level higher than that obtainable by the use of only the first inorganic filler. The second inorganic filler preferably has a mean particle size that is at least about eight times the mean particle size of the first inorganic filler.

Submicron sized inorganic filler particles also can be used alone or in combination with the aforementioned inorganic fillers. Such particles can exist as individual particles or agglomerates of individual particles. The term "submicron" is intended to denote that an individual particle has a mean particle size less than about 0.2 microns. Preferred submicron sized inorganic fillers include such materials as fumed, pyrolytic, and colloidal silicas. Such silicas may be obtained, for example, from Degussa AG (Duesseldorf, Germany) under the trademark Aerosil® OX-50. Other submicron sized inorganic fillers may include alumina or titania.

Inorganic filler particles that bear a hydroxyl group may be silanated prior to use in this invention. Silanation is well known to those skilled in the art, and any silanating compound may be used for this purpose. By "silanation" is meant chemical reaction by which some of the hydroxyl groups have been reacted with, for example, dimethyldichlorosilane to form a hydrophobic filler. The particles are typically from 50 to 95 percent silanated. Silanating agents for inorganic fillers include, but are not limited to, γ-mercaptoproyltrimethoxysilane, γ-mercaptopropyltriethoxysilane, γ-aminopropyltriethoxysilane, γ-methacryloyloxypropyltrimethoxysilane, and γ-methacryloyloxypropyltriethoxysilane.

Another class of fillers that may be used in the uncured dental composites of the present invention is organic fillers. Suitable organic fillers include prepolymerized fillers ("prepolymerized" in the sense that organic monomers have been polymerized to produce an organic resin, which, optionally, can be ground, prior to their inclusion in the uncured dental composites of this invention). Such prepolymerized fillers may be included in the uncured dental composites of the invention alone or in combination with an inorganic filler. It is preferred that the prepolymerized fillers be used in combination with an inorganic filler. Resins that could be used to make a prepolymerized filler include, but are not limited to, polymerized mono(meth)acrylic esters, polymerized poly(meth)acrylic esters, polymerized epoxy resins, polymerized unsaturated polyesters, polymerized vinyl ester resins, polymerized melamine-formaldehyde, and polymerized phenol-formaldehyde resins. The preferred resins include those made from poly(meth)acrylate esters, particularly di- and tri-(meth)acrylate esters. Uniformly-sized bead methacrylate polymers, such as Plexidon® or Plex® available from Röhm America LLC (Piscataway, N.J.), also may be utilized as organic fillers.

Another class of fillers that may be used in the uncured dental composites of the present invention is what will be referred to hereinafter as "composite fillers" (not to be confused with the "uncured dental composites" of the present invention). Composite fillers are resins that incorporate an inorganic material. One can make composite fillers by polymerizing at least one organic monomer in the presence of an inorganic filler, and comminuting the resulting material. The cured mixture can be comminuted to the desired particle size in suitable equipment, for example a grinder, ball mill, hammer mill, or vibratory mill. It may be sieved or classified to remove undesired fractions that have particle sizes that are too large or too small. A preferred mean particle size range is from about 20 to about 100 microns. Suitable organic monomers include, without limitation, monomers that are capable of polymerizing to provide polymerized mono(meth)acrylic esters, polymerized poly(meth)acrylic esters, polymerized epoxy resins, polymerized unsaturated polyesters, polymerized vinyl ester resins, polymerized melamine-formaldehyde, and polymerized phenol-formaldehyde. The preferred monomers are poly(meth)acrylate esters, particularly di- and tri-(meth)acrylate esters. Compounds of Formula I or Formula V or the (meth)acrylated hyperbranched polyester polyol of the present invention may be particularly useful. Composite fillers may be used alone or in combination with inorganic fillers, the latter being preferred.

In some applications, it may be desirable to combine different classes of fillers, e.g., inorganic with organic, inorganic with composite, organic with composite, or inorganic with both organic and composite. Regardless of whether the fillers are inorganic, organic, composite, or combinations thereof, it may be desirable, for example, to combine fillers having a mean particle size of about 0.05 to 0.2 microns with fillers having a mean particle size of about 0.5 to 15 microns. The former particle size fillers include, without limitation, fumed or colloidal silica. Alternatively, it may be preferred to use combinations of only fillers having a mean particle size between 0.5 and 15 microns, or combinations of only fillers having a mean particle size between 0.05 and 0.2 microns. Any of the above combinations of filler sizes can be further combined with fillers having a mean particle size that is at least about eight times the mean particle size of the filler having a mean particle size between 0.5 and 15 microns, thereby providing a composition with high total filler level.

Using combinations of mixed particle size fillers may enable high total filler level, and this may, in turn, help to reduce polymerization shrinkage of the uncured dental composite, without sacrificing acceptable mechanical properties of the cured dental composite.

The total amount of filler in the uncured dental composites of the present invention can range from about 20 weight percent to about 90 weight percent, preferably from about 40 weight percent to about 90 weight percent, and more preferably from about 50 weight percent to about 85 weight percent. The percentages are based on the total weight of the uncured dental composite.

Additional Optional Ingredients

In addition to the components described above, the composite material may contain additional, optional ingredients. These may comprise activators, pigments, radiopaquing agents, stabilizers, antioxidants, and other materials.

Various combinations of pigments may be used to provide suitable color match with the surrounding tooth color.

Preferred radiopaquing agents include those substances that are suitable for providing radiopacity, thereby making the cured dental composites of this invention visible on conventional X-ray film.

Preferred stabilizers (to prolong shelf life by preventing polymerization of the uncured composite) can include, for example, hydroquinone, hydroquinone monomethyl ether, 4-tert-butylcatechol, and 2,6-di-tert-butyl-4-methylphenol.

The uncured dental composite material of the present invention can be prepared using any mixing means known in the art. Such methods include, but are not limited to, roll mills, vibratory mixers, sigma mixers, planetary mixers, SpeedMixers™ (from Flack Tek, Inc., Landrum, S.C.), extruders, Buss Kneaders (Coperion Holding GmbH, Stuttgart, Germany), and Brabender Plasticorders® (Intellitorque, Brabender, Hackensack, N.J.). It is important to ensure homogeneous distribution of filler and prevent agglomeration of the finest particles that may be present. The uncured dental composite material may be packaged in any container commonly used, such as a syringe or compule.

The dental composite materials of the present invention can be used to fill cavities in teeth. Other treatments may include preventative, restorative, or cosmetic procedures in teeth. Typically, without limiting the method to a specific order of steps, the dental composite materials are placed on dental tissue, either natural or synthetic, cured, and shaped as necessary to conform to the target dental tissue. Dental tissue includes, but is not limited to, enamel, dentin, cementum, pulp, bone, and gingiva.

The dental composite materials may also be useful as dental adhesives, primers, bonding agents, pit and fissure sealants, cements, denture base and denture reline materials, orthodontic splint materials, and adhesives for orthodontic appliances. The materials also may be useful for making bridges, crowns, inlays, onlays, laminate veneers, and facings. The materials of the invention also may be useful for prosthetic replacement or repair of various hard body structures such as bone and also may be useful for reconstructive purposes during surgery, especially oral surgery.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations

The meaning of abbreviations is as follows: "hr" means hour(s), "min" means minute(s), "s" means second(s), L means liter(s), "mL" means milliliter(s), "cm" means centimeter(s), "mm" means millimeter(s)," µm" means micrometer(s), "nm" means nanometer(s), "g" means gram(s), "mol" means mole(s), "N" means Newton(s), "rpm" means revolutions per minute, "wt %" means weight percent(age), "mW" means milliwatt(s), "Mn" means number average molecular weight, "MAEW" methacrylate equivalent weight (grams/equivalent), "HOEW" means (hydroxyl equivalent weight (grams/equivalent), "MPa" means mega Pascal(s), "MHz" means megahertz, "std dev" means standard deviation, "d50" means 50% of particles have a diameter below a given size, "MEHQ" means 4-methoxyphenol, "PTFE" means polytetrafluoroethylene, "THF" means tetrahydrofuran, "DMSO" means dimethyl sulfoxide, "DMAC" means N,N-dimethylacetamide, "NEt$_3$" means triethylamine, "Ac" means the acetyl radical CH$_3$CO—, "Ac$_2$O" means acetic anhydride, "EtOAc" means ethyl acetate, "NMR" means nuclear magnetic resonance (spectroscopy), "IR" means infrared (spectroscopy), "ATR" means attenuated total reflectance, "MALDI" means matrix-assisted laser desorption/ionization mass spectrometry, "TLC" means thin layer chromatography, "GC" means gas chromatography, "THPE" means 1,1,1-tris(p-hydroxyphenyl)ethane, "THPE GE" means 1,1,1-tris(p-hydroxyphenyl)ethane triglycidyl ether, "Bis-GMA" means bisphenol-A-glycidyl methacrylate, "TEGDMA" means triethylene glycol dimethacrylate, "DMP" means dimethylol propionic acid, "CQ" means camphorquinone, and "EDB" means ethyl 4-dimethylaminobenzoate.

Materials 1,1,1-tris(p-hydroxyphenyl)ethane ("THPE"), and 1,1,1-tris(p-hydroxyphenyl)ethane triglycidyl ether ("THPE GE") were obtained from E. I. du Pont de Nemours & Co., Inc. (Wilmington, Del.). Mono-2-(methacryloyloxy)ethyl succinate, mono-2-(methacryloyloxy)ethyl maleate, and mono-2-(methacryloyloxy)ethyl phthalate were obtained from Aldrich Chemical Company (Milwaukee, Wis.).

Prostab® 5415 was obtained from Ciba (Wilmington, Del.). Tin (II) di-(2-ethylhexanoate), caprolactone, dimethylol propionic acid, pentaerythritol, n-propylamine (98%, catalogue # 109819), 3-(trimethoxysilyl)propyl methacrylate (98%, catalogue # 440159), and glass spheres, hollow (mean diameter 9-13 µm, specific gravity 1.100, catalogue # 440345) were obtained from Aldrich Chemical Company (Milwaukee, Wis.). Toluene was obtained from EMD Chemicals (Gibbstown, N.J.). Bisphenol-A-glycidyl methacrylate adduct ("Bis-GMA") was obtained from EssTech (Essington, Pa.), product code X 950-0000. Triethylene glycol dimethacrylate ("TEGDMA") was obtained from EssTech (Essington, Pa.), product code product code X 943-7424, inhibited with hydroquinone (50-70 ppm). Photosensitizers were obtained from Aldrich Chemical Company (Milwaukee, Wis.): camphorquinone (97%, catalogue #12,489-3) and ethyl 4-dimethylaminobenzoate (99+%, catalogue #E2, 490-5). Aerosil® OX-50 fumed silica was obtained from Degussa (Dusseldorf, Germany). Schott 8235 UF1.5 glass powder was obtained from Schott AG (Mainz, Germany); it had a mean diameter, d50, of 1.5 µm and was treated with $C_{10}H_{20}O_5Si$ to a level of 2.3 wt % silane.

Sample Preparation

Uncured compositions intended for testing were packed into a stainless steel 2 mm thick mold with at least one 2 mm×25 mm opening to enable two sides of the uncured composition to be exposed. The packed mold was sandwiched on either side with a polyester film, followed a glass plate. A bar of each uncured composition was cured for 60 sec. per side at 550 mW/cm$^2$.

Analytical Methods

Molecular weight was determined by gel permeation chromatography (GPC) in THF using polystyrene standards.

Differential Scanning Calorimetry (DSC) was used to measure glass transition temperature (Tg) and was measured at a heating rate of 10° C./min.

The degree of monomer polymerization ("conversion") was measured by Fourier Transform Infrared (FTIR) spectroscopy, using the total attenuated reflectance (ATR) method. The absorbances of the IR peaks at 1610 cm$^{-1}$ (corresponding to aromatic C=C stretch) and 1640 cm$^{-1}$ (corresponding to methacrylate C=C stretch) were measured before and after irradiation. The peak absorbances were all normalized using appropriate baselines, and a % C=C value and a DC value were calculated according to the equations below, using normalized absorbance values:

% C=C=[(A$_{1640}$/A$_{1610}$)after/(A1640/A$_{1610}$)before]×100 DC (degree of conversion)=100−% C=C The DC is referred to as the "C-Peak" degree of conversion.

The so-called "E-Peak" degree of conversion was also measured as described in *Dental Materials* (1990), 6(4), 241-249. This alternative method uses the ratio of the 1640 cm$^{-1}$ and the 1580 cm$^{-1}$ peaks, rather than the 1640 cm$^{-1}$ and 1610 cm$^{-1}$ peaks. The baseline of the 1640 cm$^{-1}$ peak is defined by drawing a baseline from the value at 1660 cm$^{-1}$ to the value at about 1590 cm$^{-1}$.

The percent methacrylation of the hyperbranched polyester polyol was measured by $^1$H NMR and IR spectroscopy. This method for measuring percent methacrylation has been described in, for example, Culbertson (*J. Macromol. Sci. Pure Appl. Chem.* (2002), A39(4), 267-286), and uses the absence of the O—H stretch near 3500 cm$^{-1}$ to indicate a fully methacrylated polyol. This method was employed in combination with $^1$H NMR spectroscopy in the examples that follow. A fully methacrylated polyol was prepared using an excess of methacrylating agent. The fully methacrylated polyol was analyzed using $^1$H NMR spectroscopy. The area under the peak corresponding to the allylic CH$_3$ of the methacrylate group at 1.8 ppm (DMSO-d$_6$) was determined. The area of under the peak corresponding to the caprolactone alpha CH$_2$ group at 2.2 ppm also was determined.

A ratio, Y, characteristic of the fully methacrylated product is defined as:

$$Y=[\text{area CH}_3 \text{ at 1.8 ppm/area caprolactone CH}_2 \text{ at 2.2 ppm}]_{full}$$

Then, a partially methacrylated product was prepared and the areas under the same two peaks were determined. A new ratio, X, characteristic of the partially methacrylated product is defined as:

$$X=[\text{area CH}_3 \text{ at 1.8 ppm/area caprolactone CH}_2 \text{ at 2.2 ppm}]_{partial}$$

The % methacrylation is then defined as:

$$\% \text{ methacrylation}=(X/Y)\times 100.$$

An "acid number" was determined as follows. The substance to be tested was dissolved in a suitable neutral solvent. The resulting solution was titrated with standard potassium hydroxide solution to a phenolphthalein or thymolphthalein endpoint. The acid number is expressed as the number of milligrams of potassium hydroxide required to neutralize one gram of the substance.

Fracture toughness ($K_{IC}$), flexural strength (ISO 4049), and density were determined on (2 mm×2 mm×25 mm) bars that were molded using the stainless steel mold described above. The molded bars were cured in the mold by irradiating each exposed side for 1 minute using either a) an array of three Dentsply Spectrum 800 dental lamps at 550 mW/cm$^2$, or b) a Fusion UV Systems curing unit equipped with a Q-bulb (designed for emitting light at a wavelength suitable for camphorquinone excitation).

The metal mold was covered on both sides with a 3-mil (76-micron) polyester film to exclude oxygen.

The fracture toughness test was based on both the ASTM polymers standard (ASTM D5045) and the ASTM ceramics standard (ASTM C1421, precracked beam method). Testing was conducted at a test speed of 0.5 mm/min at room temperature and ambient humidity using a three-point bend fixture (span to depth ratio of 10). The specimens were molded using the flex bar mold specified in ISO 4049. The specimens were precracked halfway through their depth. Two modifications to the test procedures were made. The first was the use of smaller test specimens than those recommended in the ASTM C1421 standard (2 mm×2 mm×25 mm instead of the recommended minimum dimensions of 3 mm×4 mm×20 mm). The second was the use of a slitting circular knife to machine the precracks. The knife was 0.31 mm in thickness with a 9 single bevel. The modified test procedures produced precracks that were equivalent to precracks produced using the techniques recommended in ASTM D5045.

The percent shrinkage (% S) was determined by measuring the densities of uncured dental composites and of bars of cured dental composites. The densities were measured with an AccuPyc 1330 Helium Pycnometer (Micromeritics Instrument Corporation, Norcross, Ga.). An uncured mixture of dental composite was placed in a PTFE mold having a 2 mm depth into which a 4×25 mm opening was made, thereby exposing two sides of a bar of the uncured dental composite. The mold was covered on either side with both a polyester sheet, followed by a glass plate. Three dental curing lamps (model Spectrum 800 from Dentsply, set at a visible light intensity of 550 mW/cm$^2$), were aligned above and parallel to the length of the bar. Each bar was cured for 2 min on its first side and then 2 min on its second side.

The density of the uncured dental composite was determined by measuring the volume of a known weight of composite. Briefly, the pycnometer was set up for 10 purges and 5 volume measurements per sample. The pycnometer cell had a volume of 1 cubic centimeter. For the uncured composite material, a liner made from aluminum foil was used to prevent the composite adhering to the cup of the pycnometer. The volume of the aluminum foil was subtracted from the volume of the uncured dental composite. The density of uncured composite $\rho_{uncured}$ is defined as grams of uncured composite divided by volume of uncured composite in cubic centimeters.

The density of the cured dental composite was measured in a similar manner as described above, except that an aluminum foil liner was not used. The density of uncured composite $\rho_{cured}$ is defined as grams of cured composite divided by volume of cured composite in cubic centimeters.

The percent shrinkage (% S) was calculated from the formula, $$[(\rho_{cured}-\rho_{uncured})/(\rho_{cured})]\times 100=\% \text{ S}.$$

Example 1

Synthesis of the Compound of Formula I Wherein each R$^1$ is methyl, each R$^2$ is —CH$_2$CH$_2$—, each R$^3$ is H, R$^7$ is methyl, and A is —[O—R$^6$]$_n$— where R$^6$ is —CH$_2$CH$_2$—, and n is 1 (hereinafter "THPE GE Succinate HEMA")

A 1 L three neck flask equipped with a mechanical stirrer, condenser, thermocouple, and addition funnel was charged with THPE GE (50 g, 0.105 mol), mono-2-(methacryloyloxy) ethyl succinate (77.6 g, 0.338 mol), triethylamine (1.0 g, 0.01 mol), and Prostab® 5415 (0.05 g,). The mixture was heated to 80° C. to obtain a pale yellow solution. The solution was stirred under nitrogen for 1 hour at 80° C. TLC (silica gel, 1/1 EtOAc/hexane) indicated no THPE GE remaining. The mixture was allowed to cool to 50° C. and then 500 mL EtOAc was added. The solution was washed with water (125 mL), saturated NaCl solution (100 mL), and then dried over MgSO$_4$. Solvent was removed in vacuo at 50° C./0.5 torr for 2 hours to give 119.7 g (98.8%) of the desired product as a pale yellow viscous oil. $^1$H NMR (500 MHz, CDCl$_3$) δ 1.93 (s, 9H), 2.08 (s, 3H), 2.61-2.7 (m, 12H), 3.8-4.2 (m, 15H), 4.3-4.4 (m, 12H), 5.6 (m, 3H), 6.1 (m, 3H), 6.75 (m, 6H), 6.98 (m, 6H); $^{13}$CNMR (125 MHz, CDCl$_3$) δ 18.2, 29.1, 30.7, 44.7, 50.2, 50.6, 62.3, 65.7, 68.4, 113.8, 125.9, 129.6, 135.8, 142.2, 156.5, 167.1, 171.9, 172.1, 176.2.

Example 2

Synthesis of the Compound of Formula I Wherein each $R^1$ is methyl, each $R^2$ is —$CH_2CH_2$—, each $R^3$ is Ac, $R^7$ is methyl, and A is —$[O—R^6]_n$— where $R^6$ is —$CH_2CH_2$—, and n is 1 (hereinafter "THPE GE Succinate HEMA Ac")

A 1 L three neck flask equipped with a mechanical stirrer, condenser, thermocouple, and addition funnel was charged with THPE GE succinate HEMA that had been prepared as in Example 1 (100 g, 0.086 mol), acetic anhydride (35 g, 0.344 mol), pyridine (3.4 g, 0.043 mol), and Prostab 5415 (0.3 g). The orange solution was stirred for 3 hours at 60° C. It was allowed to cool to room temperature and then taken up in EtOAc (300 mL), washed with saturated $NaHCO_3$ (125 mL, then 250 mL, let stir for 45 min), 10% HCl (2×100 mL), water (100 mL), saturated NaCl (100 mL), and then dried over $MgSO_4$. Solvent was removed in vacuo on to 500 mL silica gel. The composite was applied to 700 mL silica in a 2 L coarse frit funnel and eluted with 1 L hexanes, 3 L 4/1 hexanes/EtOAc, 2 L 2/1 hexanes/EtOAc, 2 L 1/1 hexanes/EtOAc, and 2 L EtOAc. The fractions at Rf 0.33 (silica gel, 1/1 hexanes/EtOAc) were collected and concentrated in vacuo to give 52.6 g (47%) of the product as a pale orange oil. $^1$H NMR (500 MHz, $CDCl_3$) δ 1.93 (s, 9H), 2.04 (s, 3H), 2.06 (s, 9H), 2.63 (m, 12H), 4.05-4.4 (m, 24 H), 5.3 (m, 3H), 5.55 (m, 3H), 6.1 (m, 3H), 6.75 (d, 6H), 6.98 (d, 6H); $^{13}$CNMR (125 MHz, $CDCl_3$) δ 20.69, 20.99, 28.86, 50.68, 62.28, 62.43, 65.92, 65.99, 113.83, 126.03, 129.64, 135.92, 142.32, 156.32, 167.04, 167.04, 170.22, 171.81.

Example 3

Synthesis of the compound of formula I wherein each $R^1$ is methyl, each $R^2$ is —CH=CH—, each $R^3$ is H, $R^7$ is methyl, and A is —$[O—R^6]_n$— where $R^6$ is —$CH_2CH_2$—, and n is 1 (hereinafter "THPE GE Maleate HEMA")

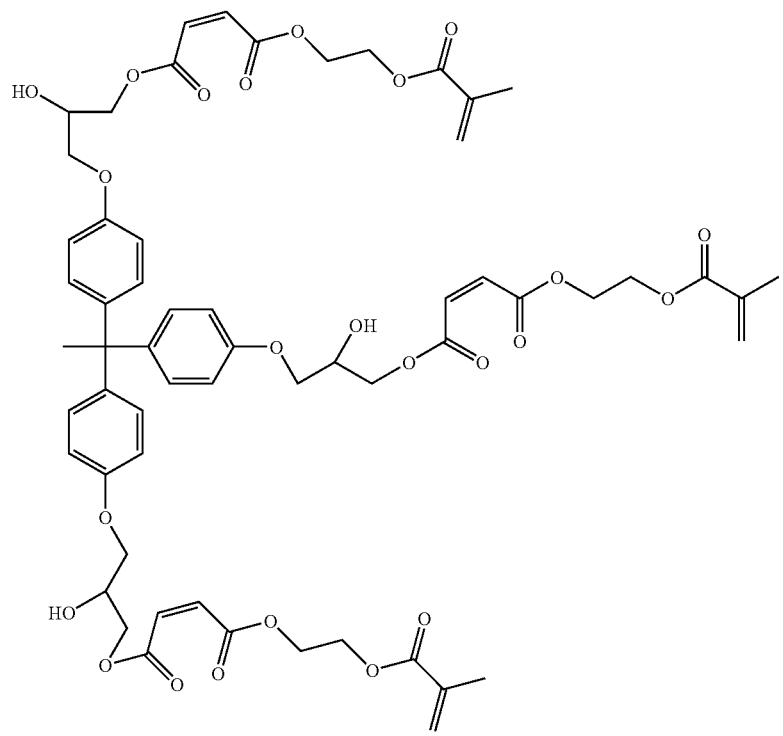

THPE GE Maleate HEMA

A 1 L three neck flask equipped with a mechanical stirrer, condenser, thermocouple, and addition funnel was charged with THPE GE (50 g, 0.105 mol), mono-2-(methacryloyloxy) ethyl maleate (77 g, 0.338 mol), triethylamine (1.0 g, 0.01 mol) and Prostab® 5415 (0.05 g). The mixture was heated to 80° C. to obtain a pale yellow solution. The solution was stirred under nitrogen for 1 hour at 80° C. TLC (silica gel, 1/1 EtOAc/hexane) indicated no THPE GE remaining. The mixture was allowed to cool to 50° C. and then 500 mL EtOAc was added. The solution was washed with water (125 mL), then saturated NaCl (100 mL), and then dried over $MgSO_4$. Solvent was removed in vacuo at 50° C./0.5 torr for 2 hours to give 128 g of the desired product as a pale yellow viscous oil. $^1$H NMR (500 MHz, $CDCl_3$) δ 1.8 (m, 9H), 1.92 (m, 3H), 3.8-4.4 (m, 27H), 5.4 (m, 3H), 6.0 (m, 3H), 6.1 (m, 6H), 6.6 (m, 6H), 6.8 (m, 6H).

Example 4

Synthesis of the Compound of Formula I Wherein each $R^1$ is methyl, each $R^2$ is —$C_6H_4$—, each $R^3$ is H, $R^7$ is methyl, and A is —$[O-R^6]_n$— where $R^6$ is —$CH_2CH_2$—, and n is 1 (hereinafter "THPE GE Phthalate HEMA")

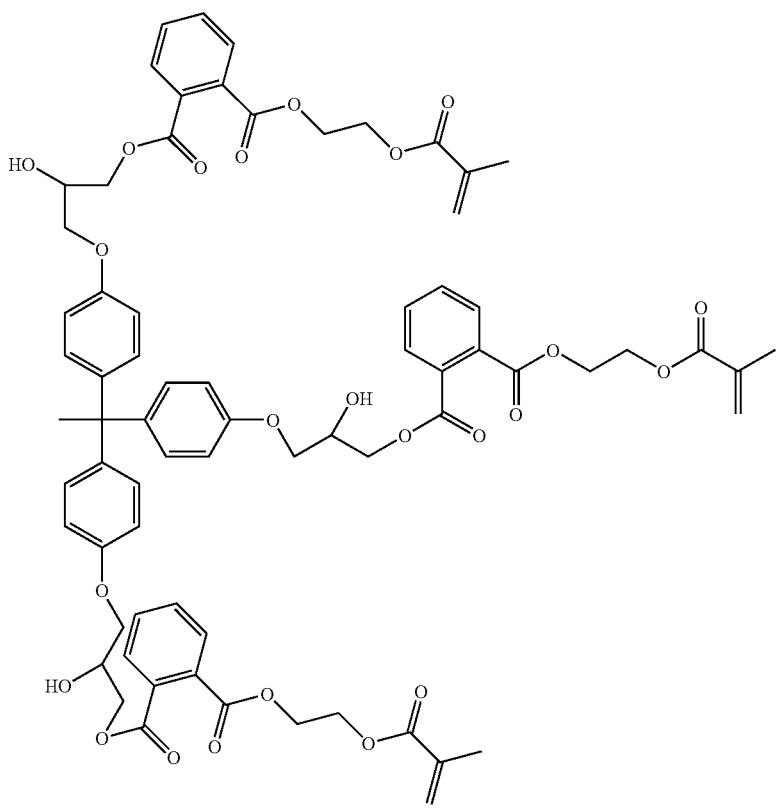

THPE GE Phthalate HEMA

A 1 L three neck flask equipped with a mechanical stirrer, condenser, thermocouple, and addition funnel was charged with THPE GE (50 g, 0.105 mol), mono-2-(methacryloyloxy) ethyl phthalate (94 g, 0.338 mol), triethylamine (1.0 g, 0.01 mol) and Prostab® 5415 (0.05 g). The mixture was heated to 80° C. to obtain a pale yellow solution. The solution was stirred under nitrogen for 1 hour at 80° C. TLC (silica gel, 1/1 EtOAc/Hexane) indicated no THPE GE remaining. The mixture was allowed to cool to 50° C. and then 500 mL EtOAc was added. The solution was washed with water (125 mL), then saturated NaCl (100 mL), and then dried over $MgSO_4$. Solvent was removed in vacuo at 50° C./0.5 torr for 2 hours to give 142 g of the desired product as a pale yellow viscous oil.

$^1$H NMR (500 MHz, $CDCl_3$) δ 1.8 (m, 9H), 1.97 (m, 3H), 3.8-4.4 (m, 27H), 5.5 (m, 3H), 6.0 (m, 3H), 6.7 (m, 6H), 6.9 (m, 6H), 7.4-7.7 (m, 12H).

Example 5 (Comparative)

Synthesis of THPE PO MA

THPE PO MA was synthesized according to the method of B. Culbertson et al., *J. Macromol. Sci. Pure Appl. Chem.* (2002), A39(4), 251-265.

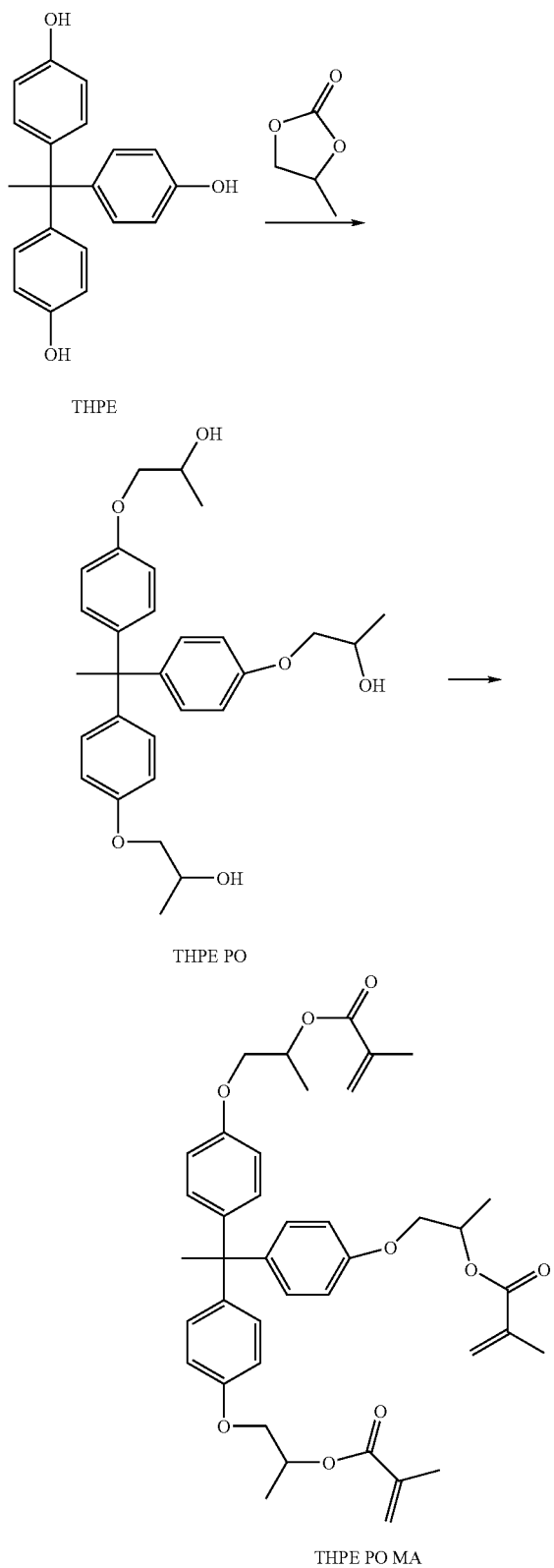

THPE

THPE PO

THPE PO MA

A. Preparation of THPE PO (in DMAC Solvent)

A 1000 mL three neck flask equipped with a mechanical stirrer, condenser, thermocouple, and addition funnel was charged with THPE (50 g, 0.16 mol), propylene carbonate (66.2 g, 0.65 mol), 2-methylimidazole (1.3 g, 0.016 mol), and DMAC (200 mL). The solution was heated to 154° C. using a heating mantle and held for four hours. The brown solution was allowed to cool to 100° C. and 250 mL water was then added through the condenser to give a reddish solution. On cooling to room temperature, and oily layer formed at the bottom of the flask. The liquid layer was decanted off and the oil taken up in acetone (100 mL) and heated to reflux. To the solution was added 300 mL water. An oil layer again separated at the bottom of the flask. The liquid was decanted off and oil taken up in 400 mL $CH_2Cl_2$ and dried over $MgSO_4$. Solvent was removed in vacuo to give 68.2 g (87%) of the desired product as a thick, tacky oil. We discovered that the oil solidified on trituration with diethyl ether to give a white solid. $^1$H NMR (500 MHz, $CDCl_3$) δ 1.35 (d, 9H), 2.18 (s, 3H), 2.37 (br s, 3H), 3.85 (m, 3H), 4.00 (m, 3H), 4.3 (m, 3H), 6.8 (m, 6H), 7.06 (m. 6H); $^{13}$C NMR (125 MHz, $CDCl_3$) δ 18.7, 50.7, 66.3, 73.3, 113.8, 129.9, 142.2, 156.6.

B. Preparation of THPE PO MA from THPE PO

A 250 mL three neck flask equipped with a mechanical stirrer, condenser, thermocouple, and addition funnel was charged with THPE PO (25 g, 0.052 mol), methacrylic anhydride (32 g, 0.21 mol), pyridine (16.5 g, 0.21 mol), and Prostab® 5415 (0.08 g). The milky pale yellow slurry was heated to 80° C. and stirred for 6.5 hours. The solution was cooled to room temp. and 150 mL EtOAc and 100 mL saturated $NaHCO_3$ was slowly added. The organic layer was washed with 100 mL saturated $NaHCO_3$, 2×100 mL 10% HCl, then saturated NaCl and dried over $MgSO_4$. Removal of solvent in vacuo (0.5 torr and 50° C.) gave 39.1 g thick yellow oil. The oil was taken up in diethyl ether (200 mL) and washed 2×100 mL saturated $NaHCO_3$, saturated NaCl, and dried over $MgSO_4$. Removal of diethyl ether in vacuo gave 36.3 g (100%) thick yellow viscous oil. $^1$H NMR (500 MHz, $CDCl_3$) δ 1.31 (d, 9H), 1.85 (m, 9H), 2.0 (s, 3H), 3.91 (m, 3H), 3.98 (m, 3H), 5.21 (m, 3H), 5.4 (m, 3H), 6.0 (m, 3H), 6.7 (m, 6H), 6.9 (m, 6H).

Example 6 (Comparative)

Synthesis of THPE GE MA

A 1 L three neck flask equipped with a mechanical stirrer, condenser, thermocouple, and addition funnel was charged with THPE GE (100 g, 0.21 mol), methacrylic acid (90.7 g, 1.05 mol), triethylamine (10.6 g, 0.10 mol) and Prostab® 5415 (0.1 g). The mixture was heated to 80° C. to obtain a pale yellow solution. The solution was stirred under nitrogen for 2 hours at 80° C. TLC (silica gel, 1/1 EtOAc/hexane) indicated no starting material remaining. The mixture was allowed to cool to 50° C. and then 500 mL EtOAc was added. To the solution was slowly added saturated $NaHCO_3$ (200 mL). The layers were separated and washed again with $NaHCO_3$ (200 mL). The combined organic layers were washed with 10% HCl, saturated $NaHCO_3$, saturated NaCl, and then dried over $MgSO_4$. Solvent was removed in vacuo at 50° C./0.5 torr for 1 hour to give 157 g of the desired product as a pale yellow viscous oil. $^1$H NMR (500 MHz, $CDCl_3$) δ 1.87 (m, 9H), 2.0 (s, 3H), 2.63 (br s, 3H), 3.9-4.3 (m, 15H), 5.5 (m, 3H), 6.1 (m, 3H), 6.7 (m, 6H), 6.9 (m, 6H); $^{13}$C NMR (125 MHz, $CDCl_3$) δ 18.3, 30.7, 50.7, 65.6, 68.6, 68.7, 113.9, 126.2, 129.6, 135.9, 142.2, 156.4, 167.1.

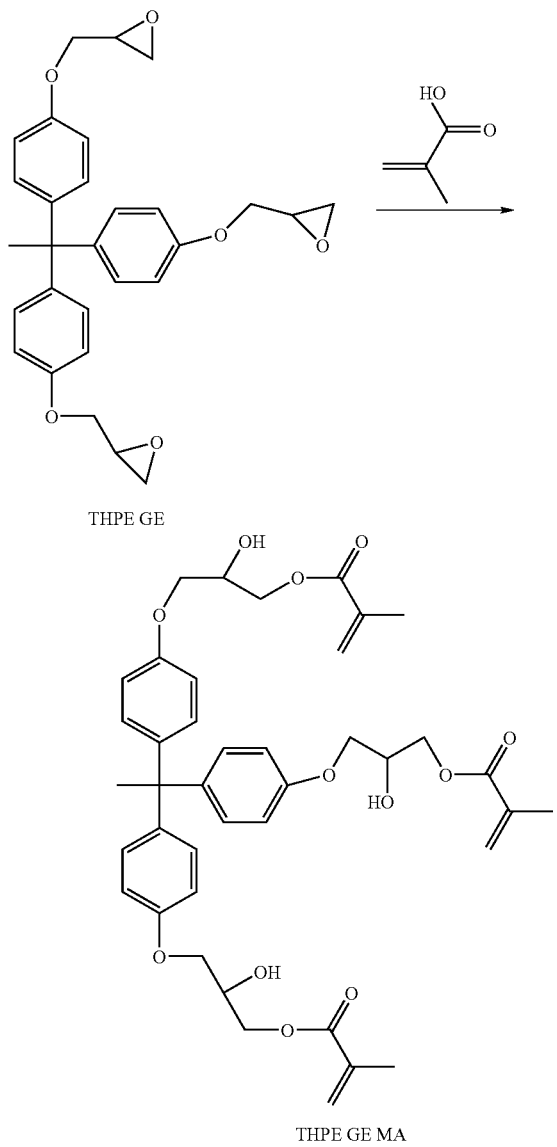

Examples 7-9 (Comparative) and 10-13

Dental Composite Materials Made with Compounds of Formula I

The following procedure was used to prepare the dental composite materials used in Comparative Examples 7-9 and Examples 10-13. In each case, the polymerizable (meth) acrylic ester component was made up of a first component, which was either Bis-GMA or one of the compounds prepared in Examples 1-4 and Comparative Examples 5-6; and a second component, here, TEGDMA.

To a "max 60" size cup of a Flack Tek SpeedMixer™ was added:

7.0 g of the first component,
3.0 g of the second component,
2.0 g of Aerosil® OX-50 fumed silica,
28.0 g of Schott 8235 UF1.5 glass powder,
0.12 g of ethyl 4-dimethylaminobenzoate ("EDB"), and
0.12 g of camphorquinone ("CQ").

The contents were mixed for three 30-second intervals at 3000 rpm. After a brief cooling period (10 minutes), the contents were mixed for an additional 30 s at 3000 rpm. The resulting paste was stored refrigerated in a yellow light room to prevent premature curing.

The paste was formed into bars, cured, and tested as described above. Results are presented in Table 1. The samples produced using compounds of the structure I (Examples 10-13) exhibited better flexural strength and fracture toughness than the comparative materials.

TABLE 1

|  | Ex. 7 (Comp) | Ex. 8 (Comp) | Ex. 9 (Comp) | Ex. 10 | Ex. 11 | Ex. 12 | Ex. 13 |
|---|---|---|---|---|---|---|---|
| First Component | | | | | | | |
| THPE GE Su HEMA (g) | | | | 7.0 | | | |
| THPE GE Su HEMA Ac (g) | | | | | 7.0 | | |
| THPE GE Maleate HEMA (g) | | | | | | 7.0 | |
| THPE GE Phth HEMA (g) | | | | | | | 7.0 |
| THPE PO MA (g) | 7.0 | | | | | | |
| THPE GE MA (g) | | 7.0 | | | | | |
| Bis-GMA (g) | | | 7.0 | | | | |
| Second Component | | | | | | | |
| TEGDMA (g) | 3.0 | 3.0 | 3.0 | 3.0 | 3.0 | 3.0 | 3.0 |
| Initiators and Fillers | | | | | | | |
| Camphorquinone (g) | 0.13 | 0.13 | 0.13 | 0.13 | 0.13 | 0.13 | 0.13 |
| ethyl-4-dimethylamino | 0.13 | 0.13 | 0.13 | 0.13 | 0.13 | 0.13 | 0.13 |

TABLE 1-continued

|  | Ex. 7 (Comp) | Ex. 8 (Comp) | Ex. 9 (Comp) | Ex. 10 | Ex. 11 | Ex. 12 | Ex. 13 |
|---|---|---|---|---|---|---|---|
| benzoate (g) |  |  |  |  |  |  |  |
| Schott glass (g) | 28.0 | 28.0 | 28.0 | 28.0 | 28.0 | 28.0 | 28.0 |
| OX 50 glass (g) | 2.0 | 2.0 | 2.0 | 2.0 | 2.0 | 2.0 | 2.0 |
| Properties |  |  |  |  |  |  |  |
| Conversion % C Peak | 78 | 78 | 81 | 86 | 84 | na | 81 |
| Conversion % E Peak | 68 | 66 | 72 | 89 | 76 | na | 78 |
| Shrinkage % | 3.4 | 2.8 | 3.2 | 3.0 | 3.1 | 2.2 | 2.5 |
| Flex Strength (MPa) | 118 | 111 | 134 | 142 | 139 | 141 | 153 |
| std dev | 18 | 19 | 18 | 13 | 13 | 17 | 7 |
| Shrinkage Stress (N) | 83 | 73 | 77 | 78 | 73 | 78 | 69 |
| Fracture Toughness (MPa (m)$^{0.5}$) | 1.45 | 1.64 | 1.79 | 2.29 | 2.05 | 2.15 | 2.25 |
| std dev | 0.17 | 0.25 | 0.18 | 0.26 | 0.14 | 0.27 | 0.10 |

Example 14

Synthesis of a (Meth)Acrylated Hyperbranched Polyester Methacrylate using Methacrylic Anhydride as an End Capping Agent for a Hyperbranched Polyester Polyol Made in a Single Stage Reaction A. A 3 L flask equipped with a mechanical stirrer, thermocouple, and short path distillation head with a water condenser, and nitrogen inlet, was charged with pentaerythritol (105 g, 0.77 mol), dimethylolpropionic acid (600 g, 4.47 mol), caprolactone (600 g, 5.26 mol), tin (II) di-(2-ethylhexanoate) ($Sn(O_2CC_7H_{15})_2$), 10 g, 0.0247 mol), and xylene (60 mL). The mixture was heated at 180° C. and the reaction progress was monitored by measurement of acid number and the volume of water collected. After 8.5 hr, about 72 mL water was collected. A 1 g sample was withdrawn and dissolved in 10 mL DMSO. The acid number was determined to be 2.0 by titration with 0.1 M KOH in methanol. The heating temperature was reduced to 120° C. and cyclohexene oxide (40 g, 0.41 mol) was added. After 60 min, the acid number was determined to be 1.5. The heating was continued for 2.5 hours under a vacuum of about 30 torr. The heating temperature was increased to 180° C. and held for 5 hours under reduced pressure (~1 torr). The hot, viscous, clear polymer was poured out of the reactor to a glass jar. The acid number was determined to be 1.1. The polymer had an Mn=1,920 and a polydispersity (Mw/Mn) of 2.08 as determined by gel permeation chromatography (GPC) vs. polystyrene standards. The Tg was determined by differential scanning calorimetry to be −26° C.

B. A mixture of the hyperbranched polyester polyol product of Example 14 (13 g, 0.080 mol HO), methacrylic anhydride (15.9 g, 0.103 mol), pyridine (36.7 g, 0.464 mol) and MEHQ (0.020 g) was heated at 85° C. for 16 hours. The reaction mixture was cooled down to room temperature, diluted with 150 mL $CH_2Cl_2$, extracted twice with 30 mL 5 wt % $NaHCO_3$ solution, extracted once with 30 mL 10 wt % HCl solution, extracted once with 30 mL water, and dried over anhydrous $Na_2SO_4$. The solution was filtered and MEHQ (0.020 g) was added. The solvent and any volatiles were removed on a rotovap at 400° C. under a vacuum of about 0.5 torr to yield 13.4 g of the desired product as a white liquid. Mass spectroscopy (MALDI) and $^1H$ NMR were indicative of a fully methacrylated product. The polymer has Mn (theor.)=2,257, MAEW (theor.)=230.

Example 15

Synthesis of a (Meth)Acrylated Hyperbranched Polyester Methacrylate using Methacrylic Anhydride as an End Capping Agent for a Hyperbranched Polyester Polyol Made in a Single Stage Reaction (Hereinafter "1× 100% MA")

A. A 100 gallon reactor was charged with caprolactone (171 kg), tin(II) octanoate (1.27 kg), pentaerythritol (3.4 kg), DMP (85.5 kg), xylenes (13 kg), and heated to 69-71° C. until a solution was obtained. The solution was then heated to 170° C. with vigorous stirring and water was collected overhead until the solution reached an acid number of 3.5. The temperature was not allowed to exceed 200° C. The mixture was allowed to cool to about 25° C. and then discharged in to a barrel to obtain the desired product as a colorless, transparent, viscous liquid.

B. A mixture of the hyperbranched polyester polyol of example 17 (1×, 122 g, 1.17 mol of reactive OH), methacrylic anhydride (198 g, 1.28 mol) and pyridine (102 g, 1.29 mol) was heated to 110° C. for 4.5 hours under a dry air stream. The reaction mixture was cooled to room temperature and then slowly poured into a solution of 10% sodium carbonate (500 mL). The resulting mixture was extracted with ethyl ether (3×100 mL). The ether extracts were combined and then washed with 5% HCl (3×100 mL) and water (3×50 mL). The ether solution was next dried over anhydrous sodium carbonate. After filtering, the resulting solution was treated with MEHQ (50 mg) and then concentrated in vacuo, giving a clear, viscous oil. The oil, kept at room temperature, was further concentrated by applying a vacuum of 20 mm Hg (with filtered air-bleed) for an additional 4 h period, followed by high vacuum for 2 hours, ultimately furnishing 79 g of the product.

IR spectroscopy of the neat sample showed an absence of OH-stretching at 3514 cm$^{-1}$ relative to the starting polyol. Additionally, a strong ester peak at 1729 cm$^{-1}$ and a peak at 1638 cm$^{-1}$ representing the methacrylate double bond were noted in the IR spectrum.

Example 16

Synthesis of a (Meth)Acrylated Hyperbranched Polyester Methacrylate using Methacrylic Anhydride as an End Capping Agent for a Hyperbranched Polyester Polyol Made in a Two Stage Reaction (Hereinafter "2× 96% MA")

A. A 100 gallon reactor was charged with caprolactone (78 kg), tin(II) octoate (2.32 kg), pentaerythritol (19 kg), DMP (117 kg), xylenes (10.6 kg), and heated to 69-71° C. until a solution was obtained. The solution was then heated to 170° C. with vigorous stirring and water was collected overhead until the solution reached an acid number of 3.5. The temperature was not allowed to exceed 200° C. The solution was cooled to 129-131° C. Caprolactone (156 kg) was added to the solution with stirring over 30 minutes. The mixture may exotherm up to about 140° C. during the feed. The solution was held at 129-131° C. for two hours. The mixture was then discharged in to a barrel to obtain the desired product as a colorless, transparent, viscous liquid.

B. A 500 mL three neck flask equipped with a mechanical stirrer, condenser, addition funnel, and thermocouple was charged with 2× (100 g), Prostab® 5415 (0.5 g), methacrylic anhydride (50 g), and sodium acetate (0.5 g). The solution was heated to 75° C. and held for four hours. The mixture was allowed to cool to room temperature and the condenser and addition funnel replaced with a distillation head. The methacrylic acid and unreacted methacrylic anhydride was distilled off at a pot temperature of 55° C. and 0.1 torr. GC analysis of the distillate showed that it was methacrylic acid and methacrylic anhydride. The temperature was raised to 72° C. vacuum maintained at 0.1 Torr until no methacrylic anhydride or methacrylic acid was detected in the by GC. The mixture was allowed to cool and discharged to give the desired product as a pale yellow, clear, viscous liquid. $^1$H NMR (CDCl$_3$) showed that 96% of the hydroxyl groups with capped with methacrylate.

Examples 17 and 18

The hyperbranched polyester polyol of example 16 was used to prepare the following partially (meth)acrylated hyperbranched polyester polyol:

| Example | % OH groups methacrylated | hereinafter called |
|---|---|---|
| 17 | 54 | "2 × 54% MA" |
| 18 | 79 | "2 × 79% MA" |

Example 19

Synthesis of a Hyperbranched Polyester Methacrylate by Capping a Hyperbranched Polyester Polyol with Methacrylic Anhydride (73% Capped, Hereinafter "2× 73% MA")

A mixture of the hyperbranched polyester polyol of Example 16 (146 g, 0.685 mol of reactive OH), methacrylic anhydride (75 g, 0.49 mol) and pyridine (38 g, 0.48 mol) was heated to 110° C. for 4.5 hours under a dry air stream. The reaction mixture was cooled to room temperature and then slowly poured into a solution of 10% sodium carbonate (300 mL). The resulting mixture was stirred for two hours, diluted with ethyl acetate (500 mL) and then gently stirred overnight. The mixture was transferred to a separatory funnel and the aqueous layer (containing an emulsion enriched in OH-terminated product) was discarded. The remaining organic layer was washed with 5% HCl (3×100 mL) and water (2×100 mL) and was then dried over anhydrous sodium carbonate. After filtering, the resulting solution was treated with MEHQ (60 mg) and then concentrated in vacuo with mild heating, giving a clear viscous oil. The oil, kept at room temperature, was further concentrated by applying a vacuum of 20 mm Hg (with filtered air-bleed) for an additional 4 h period, followed by high vacuum for 12 hours, ultimately furnishing 110 g of the product.

IR spectroscopy of the neat sample showed significantly reduced OH-stretching relative to the starting polyol, with a band centered at 3540 cm$^{-1}$. Additionally, a strong ester peak at 1732 cm$^{-1}$ and a peak at 1638 cm$^{-1}$ representing the methacrylate double bond were noted in the IR spectrum. $^1$H NMR spectroscopy (in CDCl$_3$) confirmed the presence of terminal OH and terminal methacrylate groups, with a methacrylate capping level near 73%.

Example 20

Synthesis of a Hyperbranched Polyester Methacrylate by Capping a Hyperbranched Polyester Polyol with Methacrylic Anhydride (62% Capped, Hereinafter "2× 62% MA")

A mixture of the hyperbranched polyester polyol of Example 16 (106 g, 0.549 mol of reactive OH), methacrylic anhydride (42 g, 0.27 mol) and pyridine (22 g, 0.28 mol) was heated to 110° C. for 4.5 hours under a dry air stream. The reaction mixture was cooled to room temperature and then slowly poured into a solution of 10% sodium carbonate (350 mL). The resulting mixture was stirred for one hour, diluted with diethyl ether (300 mL) and then gently stirred overnight. The mixture was transferred to a separatory funnel and the aqueous layer (containing an emulsion enriched in OH-terminated product) was discarded. The remaining organic layer was washed with 5% HCl (3×100 mL) and water (2×100 mL) and was then dried over anhydrous sodium carbonate. After filtering, the resulting solution was treated with MEHQ (50 mg) and then concentrated in vacuo with mild heating, giving a clear, viscous oil. The oil, kept at room temperature, was further concentrated by applying a vacuum of 20 mm Hg (with filtered air-bleed) for an additional 4 h period, followed by high vacuum for 12 hours, ultimately furnishing 81 g of the product.

IR spectroscopy of the neat sample showed reduced OH-stretching relative to the starting polyol, with a band centered at 3538 cm$^{-1}$. Additionally, a strong ester peak at 1730 cm$^{-1}$ and a peak at 1637 cm$^{-1}$ representing the methacrylate double bond were noted in the IR spectrum. $^1$H NMR spectroscopy (in CDCl$_3$) confirmed the presence of terminal OH and terminal methacrylate groups, with a methacrylate capping level near 62%.

Example 21

Synthesis of a Hyperbranched Polyester Methacrylate by Capping a Hyperbranched Polyester Polyol with Methacrylic Anhydride (38% Capped, Hereinafter "2× 38% MA")

A mixture of the hyperbranched polyester polyol of Example 16 (126 g, 0.653 mol of reactive OH), methacrylic anhydride (33 g, 0.21 mol) and pyridine (17 g, 0.21 mol) was heated to 110° C. for 4.5 hours under a dry air stream. The reaction mixture was cooled to room temperature and then slowly poured into a solution of 10% sodium carbonate (300 mL). The resulting mixture was stirred for two hours, diluted with ethyl acetate (500 mL) and then gently stirred overnight. The mixture was transferred to a separatory funnel and the aqueous layer (containing an emulsion enriched in OH-terminated product) was discarded. The remaining organic layer was washed with 5% HCl (3×100 mL) and water (2×100 mL) and was then dried over anhydrous sodium carbonate. After filtering, the resulting solution was treated with MEHQ (50 mg) and then concentrated in vacuo with mild heating, giving a clear viscous oil. The oil, kept at room temperature, was further concentrated by applying a vacuum of 20 mm Hg (with filtered air-bleed) for an additional 4 h period, followed by high vacuum for 12 hours, ultimately furnishing 74 g of the product.

IR spectroscopy of the neat sample showed significantly reduced OH-stretching relative to the starting polyol, with a band centered at 3524 cm$^{-1}$. Additionally, a strong ester peak at 1730 cm$^{-1}$ and a peak at 1637 cm$^{-1}$ representing the methacrylate double bond were noted in the IR spectrum. $^1$H NMR spectroscopy (in CDCl$_3$) confirmed the presence of terminal OH and terminal methacrylate groups, with a methacrylate capping level near 38%.

Example 22

Synthesis of a Hyperbranched Polyester Methacrylate by Capping a Hyperbranched Polyester Polyol with Methacrylic Anhydride and Acetic Anhydride (62% Capped with Methacrylate, 38% Capped with Acetate, Hereinafter "2× 62% MA 38% Ac")

A mixture of the partially methacrylated polyester polyol prepared in Example 20 (44 g, ca. 0.19 mol of reactive OH), acetic anhydride (22 g, 0.22 mol) and pyridine (17 g, 0.21 mol) was heated to 110° C. for 4 hours under a dry air stream. The reaction mixture was cooled to room temperature and then slowly poured into a solution of 10% sodium carbonate (200 mL). The resulting mixture was stirred for one hour, diluted with diethyl ether (300 mL) and then gently stirred overnight. The mixture was transferred to a separatory funnel and the aqueous layer was discarded. The remaining organic layer was washed with 5% HCl (3×100 mL) and water (2×100 mL) and was then dried over anhydrous sodium carbonate. After filtering, the resulting solution was treated with MEHQ (20 mg) and then concentrated in vacuo with mild heating, giving a viscous, light-orange oil. The oil, kept at room temperature, was further concentrated by applying a vacuum of 20 mm Hg (with filtered air-bleed) for an additional 4 h period, followed by high vacuum for 12 hours, ultimately furnishing 30 g of the product.

IR spectroscopy of the neat sample showed a near absence of OH-stretching relative to the partially methacrylated starting material. Additionally, a broad ester peak centered at 1736 cm$^{-1}$ and a peak at 1637 cm$^{-1}$ representing the methacrylate double bond were noted in the IR spectrum. $^1$H NMR spectroscopy (in CDCl$_3$) confirmed the presence of terminal acetate groups and terminal methacrylate groups, with a methacrylate capping level near 60%.

Example 23 (Comparative)

Synthesis of Perstorp Boltorn H2004 Methacrylate (Hereinafter "Comp 23")

A mixture of Boltorn H2004 polyol (obtained from Perstorp Specialty Chemicals AB, Sweden) (83 g, 0.44 mol of reactive OH), methacrylic anhydride (73 g, 0.47 mol) and pyridine (37 g, 0.47 mol) was heated to 110° C. for 4.5 hours under a dry air stream. The reaction mixture was cooled to room temperature and then slowly poured into a solution of 10% sodium carbonate (300 mL). The resulting mixture was extracted with diethyl ether (3×100 mL). The ether extracts were combined and then washed with 5% HCl (3×100 mL), water (3×50 mL). And then brine (50 mL). The ether solution was next dried over anhydrous sodium carbonate. After filtering, the resulting solution was treated with MEHQ (40 mg) and then concentrated in vacuo, giving a clear, viscous oil. The oil, kept at room temperature, was further concentrated by applying a vacuum of 20 mm Hg (with filtered air-bleed) for an additional 4 h period, followed by high vacuum for 1 hour, ultimately furnishing 66 g of the product.

IR spectroscopy of the neat sample showed an absence of OH-stretching at 3522 cm$^{-1}$ relative to the starting polyol. Additionally, a strong ester peak at 1741 cm$^{-1}$ and a peak at 1638 cm$^{-1}$ representing the methacrylate double bond were noted in the IR spectrum.

Examples 24 (Comparative), 25, 26 (Comparative), 27, 28(Comparative), and 29

The following procedure was used to prepare the dental composite materials used in Comparative Examples 24, 26, and 28 and Examples 25, 27, and 29. In each case, the polymerizable (meth)acrylic ester component was made up of a first component, which was either Bis-GMA, THPE GE MA, or THPE PO MA; and a second component, here, either Comp 23 or 2× 96% MA.

The ingredients were mixed in a Flack Tek SpeedMixer™ as described in Examples 7-13. Except for the materials of Example 28(Comp.) and 29, which were too viscous to process, the paste was formed into bars, cured, and tested as described above. Results are presented in Table 2, in which "Ex" denotes "Example". 2× 96% MA-containing composites had higher toughness, flexural strength, and comparable shrinkage as compared to the composites made with the material of Comp 23.

TABLE 2

|  | Ex. 24 (Comp) | Ex. 25 | Ex. 26 (Comp) | Ex. 27 | Ex. 28 (Comp) | Ex. 29 |
|---|---|---|---|---|---|---|
| First Component |  |  |  |  |  |  |
| Bis-GMA (g) | 7.0 | 7.0 |  |  |  |  |
| THPE PO MA (g) |  |  | 7.0 | 7.0 |  |  |
| THPE GE MA (g) |  |  |  |  | 7.0 | 7.0 |
| Second Component |  |  |  |  |  |  |
| Comp 23 (g) | 3.0 |  | 3.0 |  | 3.0 |  |
| 2 × 96% MA (g) |  | 3.0 |  | 3.0 |  | 3.0 |
| Initiators and Fillers |  |  |  |  |  |  |
| Camphorquinone (g) | 0.13 | 0.13 | 0.13 | 0.13 | 0.13 | 0.13 |
| EDB (g) | 0.13 | 0.13 | 0.13 | 0.13 | 0.13 | 0.13 |

TABLE 2-continued

|  | Ex. 24 (Comp) | Ex. 25 | Ex. 26 (Comp) | Ex. 27 | Ex. 28 (Comp) | Ex. 29 |
|---|---|---|---|---|---|---|
| Schott glass (g) | 28.0 | 28.0 | 28.0 | 28.0 | 28.0 | 28.0 |
| OX 50 glass (g) | 2.0 | 2.0 | 2.0 | 2.0 | 2.0 | 2.0 |
| Properties |  |  |  |  |  |  |
| Bars Conversion % C Peak | 84 | 76 | 81 | 79 | ** | ** |
| Bars Conversion % E Peak | 74 | 64 | 73 | 73 | ** | ** |
| Shrinkage % | 2.16 | 2.18 | 3.01 | 2.76 | ** | ** |
| Flex Strength (MPa) | 108 | 132 | 93.5 | 96.52 | ** | ** |
| std dev | 5 | 26 | 14 | 17 | ** | ** |
| Shrinkage Stress (N) | 61.8 | 65 | 64 | 61 | ** | ** |
| Fracture Toughness (MPa (m)$^{0.5}$) | 1.55 | 1.74 | 1.01 | 1.39 | ** | ** |
| std dev | 0.14 | 0.22 | 0.15 | 0.21 | ** | ** |

** Too viscous to make testable bars.

Examples 30-33

The following procedure was used to prepare the dental composite materials used in Examples 30 through 33 of Table 3. In each example, the polymerizable (meth)acrylic ester component was made up of a first component, which was either THPE GE Succinate HEMA, or THPE GE Succinate HEMA Ac; and a second component, a methacrylated hyperbranched polyester reaction product of the current invention.

The composites of Table 3 were hand mixed. Briefly, the components were combined in a beaker, cast on to a PTFE sheet and kneaded for several minutes. The kneading process involves flattening the composite, folded it over, and then flattening it again.

The mixtures were degassed in a desiccator with vacuum pump, cycling between atmospheric pressure and full vacuum every 10 min. for 1 hour, then holding at 50 torr overnight (about 16 hr). The mixtures were further degassed for 8 hr at 45° C. in a vacuum oven at 380 torr of vacuum, with an air flow to prevent premature polymerization. The mixtures were wrapped in foil to exclude light and stored in a refrigerator until used.

Bars were prepared from the uncured composite, cured with visible light, and tested, as previously described. Results are presented in Table 3.

TABLE 3

|  | Ex. 30 | Ex. 31 | Ex. 32 | Ex. 33 |
|---|---|---|---|---|
| First Component |  |  |  |  |
| THPE GE Su HEMA (g) | 2.5 |  |  |  |
| THPE GE Su HEMA Ac (g) |  | 2.5 | 2.5 | 2.5 |
| Second Component |  |  |  |  |
| 2 × 96% MA (g) | 2.5 | 2.5 |  |  |
| 1 × 100% MA (g) |  |  | 2.5 |  |
| 2 × 62% MA 38% Ac (g) |  |  |  | 2.5 |
| Initiators and Fillers |  |  |  |  |
| Camphorquinone (g) | 0.06 | 0.06 | 0.06 | 0.06 |
| EDB (g) | 0.06 | 0.06 | 0.06 | 0.06 |
| Schott 8235 glass (g) | 14 | 14 | 14 | 14 |
| Degussa OX-50 (g) | 1 | 1 | 1 | 1 |
| Properties |  |  |  |  |
| Conversion % E Peak | 88 | 89 | 88 | 89 |
| Shrinkage % | 2.20 | 2.20 | 2.43 | 2.13 |
| Flex Strength (MPa) | 122 | 125 | 116 | 91 |
| Shrinkage Stress (N) | 64 | 69 | 71 | 67 |
| Fracture Toughness (MPa (m)$^{0.5}$) | 2.01 | 2.00 | 1.92 | 1.74 |

Table 3 shows that compounds of Formula I, combined with a (meth)acrylated hyperbranched polyester polyol of the present invention in a 50/50 ratio, based on the total weight of polymerizable (meth)acrylic ester component, provide a good balance of physical properties and low shrinkage.

Examples 34-42

A Sigma mixer ("B&P Model 2 cubic inch Horizontal Batch Mixer", B&P Process Equipment and Systems LLC, 1000 Hess Ave., Saginaw, Mich., USA) was used to prepare the dental composites in examples 34 to 42.

The procedure for preparing dental composites in a sigma mixer is as follows. The monomers, photosensitizers, and fillers were combined in a glass vessel and then transferred to the Sigma mixer that was preheated to 45° C. The sample was mixed for 15 minutes at 10 rpm at atmospheric pressure, 15 minutes at 20 rpm at atmospheric pressure, and 30 minutes at 15 rpm under a vacuum of 245 torr. Bars were prepared from the uncured composite, cured with visible light, and tested as previously described. Results are presented in Table 4.

TABLE 4

|  | Ex. 34 | Ex. 35 | Ex. 36 | Ex. 37 | Ex. 38 | Ex. 39 | Ex. 40 | Ex. 41 | Ex. 42 |
|---|---|---|---|---|---|---|---|---|---|
| First Component |  |  |  |  |  |  |  |  |  |
| THPE GE Su HEMA (g) | 3 | 3 | 5 | 7 | 7 | 4 | 6 | 4 | 6 |
| Second Component |  |  |  |  |  |  |  |  |  |
| 2 × 96% MA (g) |  | 7 | 2.5 | 3 |  | 4.75 | 1.25 | 1.25 | 2.75 |
| 2 × 38% MA (g) | 7 |  | 2.5 |  | 3 | 1.25 | 2.75 | 4.75 | 1.25 |
| Initiators and Fillers |  |  |  |  |  |  |  |  |  |
| Camphorquinone (g) | 0.13 | 0.13 | 0.13 | 0.13 | 0.13 | 0.13 | 0.13 | 0.13 | 0.13 |
| EDB (g) | 0.13 | 0.13 | 0.13 | 0.13 | 0.13 | 0.13 | 0.13 | 0.13 | 0.13 |
| Schott 8235 glass (g) | 28 | 28 | 28 | 28 | 28 | 28 | 28 | 28 | 28 |
| Degussa OX-50 (g) | 2 | 2 | 2 | 2 | 2 | 2 | 2 | 2 | 2 |

TABLE 4-continued

|  | Ex. 34 | Ex. 35 | Ex. 36 | Ex. 37 | Ex. 38 | Ex. 39 | Ex. 40 | Ex. 41 | Ex. 42 |
|---|---|---|---|---|---|---|---|---|---|
| Properties |
| Conversion % | 79 | 87 | 87 | 87 | 90 | 89 | 89 | 88 | 89 |
| Shrinkage % | 1.18 | 1.90 | 1.72 | 1.57 | 1.55 | 2.11 | 1.69 | 1.59 | 2.01 |
| Flex Strength (MPa) | 25 | 93 | 71 | 133 | 78 | 84 | 73 | 36 | 107 |
| Shrinkage Stress (N) | 47.55 | 67.58 | 63.03 | 57.37 | 56.43 | 63 | 60 | 60 | 56 |
| Fracture Toughness (MPa (m)$^{0.5}$) | 0.42 | 1.55 | 1.3 | 2.26 | 1.54 | 1.34 | 1.25 | 0.62 | 1.67 |

Table 4 shows that the use of a lower percentage of the compound of 5 Formula 1, while providing low shrinkage, provides composites with less than optimal mechanical properties. Table 4 also shows that increasing the amount of compound of Formula I to 70 percent provides materials having reasonable shrinkage with improved mechanical properties. The best example in Table 4 is Example 37, which provided the best balance of low shrinkage with optimal mechanical properties.

Examples 43-46 and Comparative Examples 47 and 48 Dental Composite Materials Made with Compounds of Formula I and MMA Dimer A. Preparation of MMA Dimer The synthesis of the MMA dimer was described in Macromolecules (1996), 29, 7717. A mixture of methyl methacrylate (1.5 liters), acetone (1.5 liters), 2,2'-azobisisobutyronitrile ("AIBN," 1.5 g) and (iPr)(H$_2$O)Co(III) DMG-BF$_2$)$_2$ catalyst (see structure below) (0.22 g) was heated at 72° C. under nitrogen for 4 hours. Solvent and residual monomer was removed on a rotary evaporator. Distillation of the residue at reduced pressure gave 156 g of the MMA dimer as a pale yellow liquid; boiling point 45-46° C. at 0.03 torr.

Structure of MMA Dimer

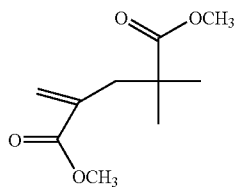

Structure of Catalyst (iPr)(H$_2$O)Co(III)(DMG-BF$_2$)$_2$

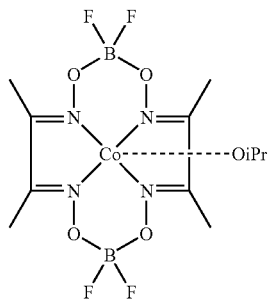

Dental composites were prepared using the same procedure as described in Examples 7-13. As a first component, monomers were selected from either Bis-GMA or a compound of Formula I, namely THPE GE Su HEMA. As a second monomer component, monomers were selected from either the MMA dimer or TEGDMA.

The uncured composite was formed into bars, cured using visible light, and tested as described above. Results are presented in Table 5.

TABLE 5

|  | Ex. 43 | Ex. 44 | Ex. 45 | Ex. 46 | Ex. 47 (comp) | Ex. 48 (comp) |
|---|---|---|---|---|---|---|
| First Component |
| Bis-GMA (g) | 9.0 |  | 7.0 |  | 7.0 |  |
| THPE GE Su HEMA (g) |  | 9.0 |  | 7.0 |  | 7.0 |
| Second Component |
| MMA dimer (g) | 1.0 | 1.0 | 3.0 | 3.0 |  |  |
| TEGDMA (g) |  |  |  |  | 3.0 | 3.0 |
| Fillers and Initiators |
| Camphorquinone (g) | 0.13 | 0.13 | 0.13 | 0.13 | 0.13 | 0.13 |

TABLE 5-continued

|  | Ex. 43 | Ex. 44 | Ex. 45 | Ex. 46 | Ex. 47 (comp) | Ex. 48 (comp) |
|---|---|---|---|---|---|---|
| ethyl-4-dimethylamino benzoate (g) | 0.13 | 0.13 | 0.13 | 0.13 | 0.13 | 0.13 |
| Schott glass (g) | 28.0 | 28.0 | 28.0 | 28.0 | 28.0 | 28.0 |
| OX 50 glass (g) | 2.0 | 2.0 | 2.0 | 2.0 | 2.0 | 2.0 |
| Properties |  |  |  |  |  |  |
| Conversion % |  | 85 |  | 77 | 84 |  |
| Shrinkage % | 2.14 | 1.44 | 1.94 | 1.39 | 3.45 | 2.81 |
| Flex Strength (MPa) |  | 149 |  | 37 | 134 | 142 |
| Fracture Toughness (MPa (m)$^{0.5}$) |  | 2.49 |  | 0.67 | 1.79 | 2.29 |

Table 5 shows that the MMA dimer can be used instead of TEGDMA. If the MMA dimer is used in high loadings, it will result in reduced polymerization shrinkage (compare example 45 with example 47, and also example 46 with 48), but the flexural strength and fracture toughness will be reduced (compare example 46 with 48). However, at low MMA dimer loadings (example 44) a good balance of low polymerization shrinkage and high flexural strength and high fracture toughness is achieved.

Examples 49 (Comparative) and 50

Dental Composite Materials Made with One Polymerizable Component

Dental composites were prepared using the same procedure as described in Examples 7-13. For the single polymerizable component, the monomer was selected from either Bis-GMA or a compound of structure 1, namely, THPE GE Su HEMA.

The viscous paste was formed into bars, cured, and tested as described above. Results are presented in Table 6. This result shows that the compounds of structure I contribute significantly higher fracture toughness than Bis-GMA alone.

TABLE 6

|  | Ex. 49 (Comp) | Ex. 50 |
|---|---|---|
| Ingredients |  |  |
| Bis-GMA (g) | 10 |  |
| THPE Ge Su HEMA (g) |  | 10 |
| Camphorquinone (g) | 0.13 | 0.13 |
| ethyl-4-dimethylamino benzoate (g) | 0.13 | 0.13 |
| Schott glass (g) | 28.0 | 28.0 |
| OX 50 glass (g) | 2.0 | 2.0 |
| Properties |  |  |
| Flex Strength (MPa) | 122 | 119 |
| Fracture Toughness (MPa (m)$^{0.5}$) | 1.41 | 2.14 |

Table 6 shows that a composite made from a compound of Formula I (as the only (meth)acrylic ester component) has higher fracture toughness than a similar composite in which Bis-GMA was the only (meth)acrylic ester component.

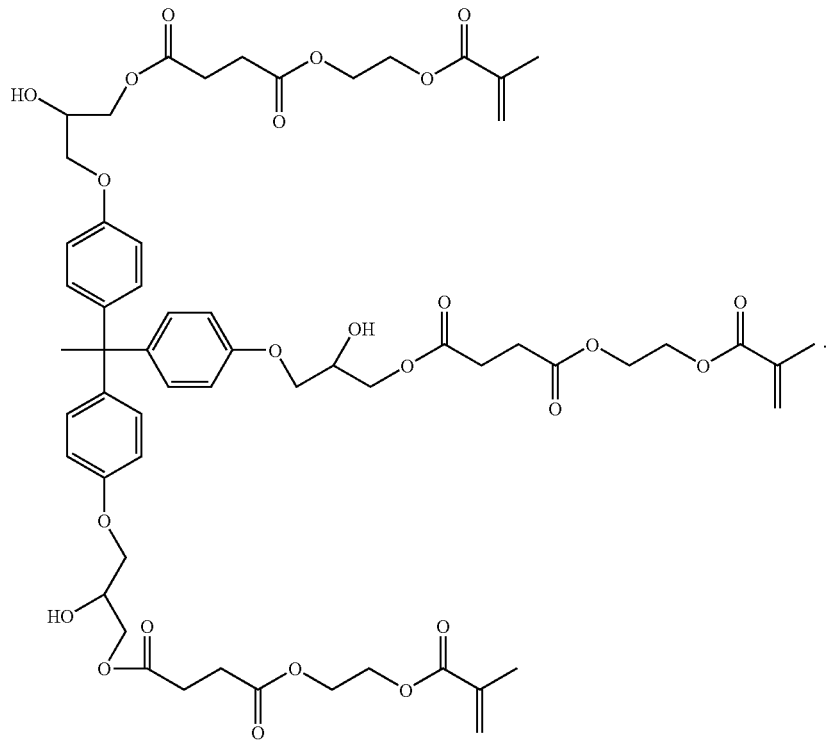

We claim:

1. An uncured dental composite material comprising:
(A) a polymerizable (meth)acrylic ester component comprising:

(1) a compound of Formula I:

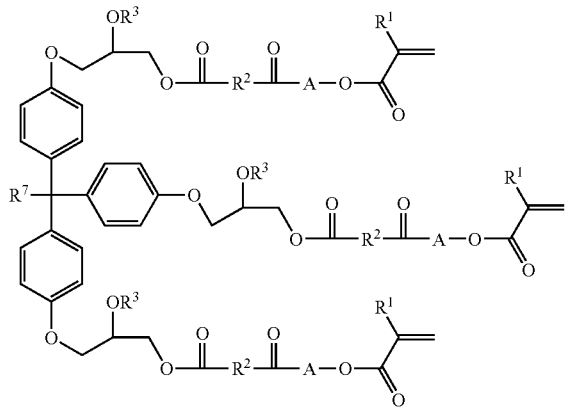

wherein:

each $R^1$ is independently hydrogen or methyl;

each $R^2$ is an alkylene having 2 to 14 carbon atoms, or an alkenylene having 2 to 8 carbon atoms, or a divalent alicyclic hydrocarbon having 5 to 14 carbon atoms, or a phenylene which is optionally substituted with halogen or an alkyl group having 1 to 5 carbon atoms;

each $R^3$ is independently selected from hydrogen, acetyl, methyl, ethyl, $C_{3-6}$ linear or branched alkyl, or benzyl;

$R^7$ is independently selected from hydrogen, methyl, ethyl, $C_{3-6}$ linear or branched alkyl, phenyl, or benzyl; and each A is a repeat unit of the formula:

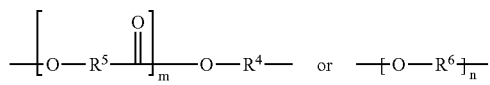

wherein:

each $R^4$ is independently an alkylene having 2 or 3 carbon atoms, each $R^5$ is independently an alkylene having 2 to 7 carbon atoms, each $R^6$ is independently an alkylene having 2 to 5 carbon atoms, m is an integer of 1 to 10, and n is an integer of 1 to 10; and (2) at least one reaction product produced by a process comprising:

(a). preparing a hyperbranched polyester polyol by heating a mixture that includes
  (i) dimethylol propionic acid;
  (ii) caprolactone; and, optionally,
  (iii) pentaerythritol;

(b). combining the product of step (a) with methacrylic anhydride, provided that the resulting degree of end capping is at least 25%, with radically polymerizable end groups constituting at least 25% of all end groups;

(B) at least one polymerization initiator compound; and (C) at least one filler.

2. The uncured dental composite material of claim 1, wherein the compound of Formula I is:

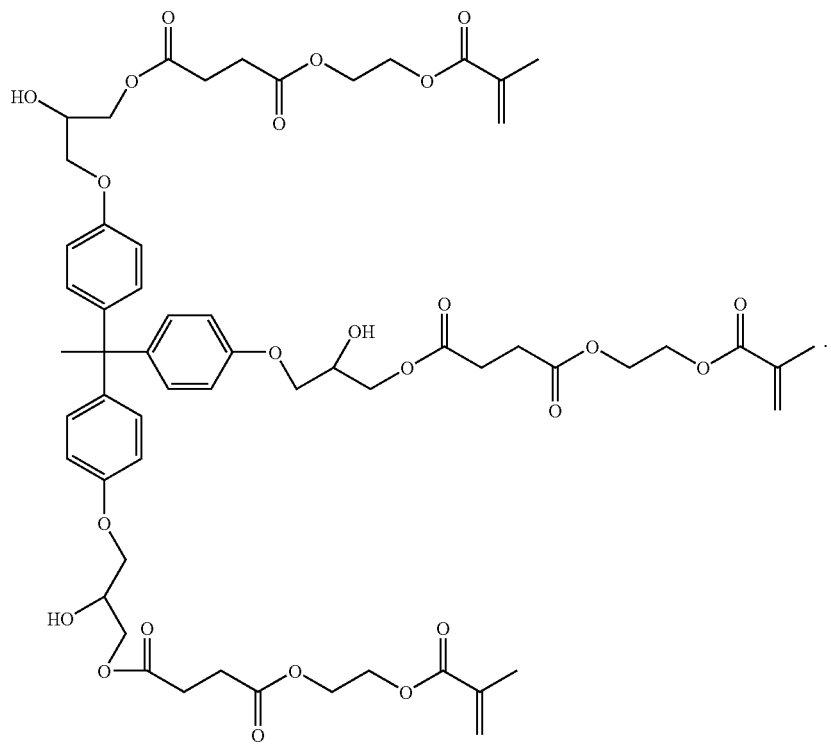

3. An uncured dental composite material comprising:
(A) a polymerizable (meth)acrylic ester component comprising:
(1) a compound of the Formula I:

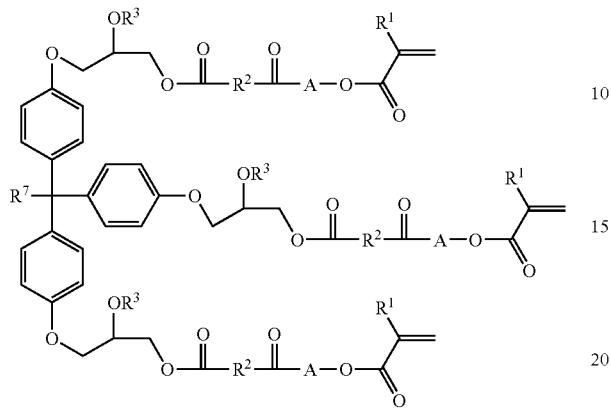

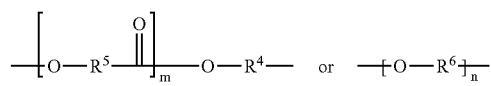

wherein:
each $R^1$ is independently hydrogen or methyl;
each $R^2$ is an alkylene having 2 to 14 carbon atoms, or an alkenylene having 2 to 8 carbon atoms, or a divalent alicyclic hydrocarbon having 5 to 14 carbon atoms, or a phenylene which is optionally substituted with halogen or an alkyl group having 1 to 5 carbon atoms;
each $R^3$ is independently selected from hydrogen, acetyl, methyl, ethyl, $C_{3-6}$ linear or branched alkyl, or benzyl;
$R^7$ is independently selected from hydrogen, methyl, ethyl, $C_{3-6}$ linear or branched alkyl, phenyl, or benzyl; and
each A is a repeating unit of the formula:

wherein:
each $R^4$ is independently an alkylene having 2 or 3 carbon atoms,
each $R^5$ is independently an alkylene having 2 to 7 carbon atoms,
each $R^6$ is independently an alkylene having 2 to 5 carbon atoms,
m is an integer of 1 to 10,
and n is an integer of 1 to 10; and
(2) at least one reaction product produced by a process comprising:
(a). preparing a first intermediate reaction product by heating a mixture that includes:
(i) dimethylol propionic acid
(ii) caprolactone; and, optionally,
(iii) pentaerythritol;
(b). heating the first intermediate reaction product of step (a) with additional caprolactone to form a second intermediate reaction product; and
(c). reacting the second intermediate reaction product of step (b) with methacrylic anhydride to provide the reaction product, provided that the degree of end capping of the reaction product is at least 25%, with radically polymerizable end groups constituting at least 25% of all end groups;
(B) at least one polymerization initiator compound; and
(C) at least one filler.
4. The uncured dental composite material of claim 3, wherein the compound of Formula I is: